(12) United States Patent
Garry et al.

(10) Patent No.: US 11,127,484 B2
(45) Date of Patent: Sep. 21, 2021

(54) ANALYSIS OF SINGLE CELL TRANSCRIPTOMICS

(71) Applicant: Regents of the University of Minnesota, Minneapolis, MN (US)

(72) Inventors: Daniel J. Garry, Eagan, MN (US); Wuming Gong, Saint Paul, MN (US); Naoko Koyano, Shoreview, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 696 days.

(21) Appl. No.: 15/462,728

(22) Filed: Mar. 17, 2017

(65) Prior Publication Data

US 2017/0270241 A1    Sep. 21, 2017

Related U.S. Application Data

(60) Provisional application No. 62/309,861, filed on Mar. 17, 2016.

(51) Int. Cl.
G16B 25/00    (2019.01)
G16B 25/10    (2019.01)

(52) U.S. Cl.
CPC ............. *G16B 25/00* (2019.02); *G16B 25/10* (2019.02)

(58) Field of Classification Search
None
See application file for complete search history.

(56) References Cited

PUBLICATIONS

Jia et al. Gene Ranking of RNA-Seq Data via Discriminant Non-Negative Matrix Factorization PLoS One vol. 10 article e0137782 (Year: 2015).*
Macaulay et al. Single-Cell RNA-Sequencing Reveals a Continuous Spectrum of Differentiation in Hematopoietic Cells Cell Reports vol. 14, pp. 966-977 (Year: 2016).*
Kharchenko et al. Bayesian approach to single-cell differential expression analysis Nature Methods vol. 11, pp. 740-744 (Year: 2014).*
Tsigeiny et al. Analysis of Metagene Portraits Reveals Distinct Transitions During Kidney Organogenesis ScienceSignaling vol. 1, article ra16 (Year: 2008).*
Xiao et al. Component plane presentation integrated self-organizing map for microarray data analysis FEBS Letters vol. 538, pp. 117-124 (Year: 2003).*
Zeisel et al. Cell types in the mouse cortex and hippocampus revealed by single-cell RNA-seq Science vol. 347, pp. 1138-1142 and supplemental content pp. 1-33 (Year: 2015).*
Banerji, C. R. S., et al., "Cellular network entropy as the energy potential in Waddington's differentiation landscape", Sci. Rep. 3: 3039, (2013), 1-7.
Barnes, R., et al., "Analysis of the Hand1 Cell Lineage Reveals Novel Contributions to Cardiovascular, Neural Crest, Extra-Embryonic, and Lateral Mesoderm Derivatives", Developmental Dynamics 239, (2010), 3086-3097.
Bondue, A, et al., "Defining the earliest step of cardiovascular progenitor specification during embryonic stem cell differentiation", J. Cell Biol. 192, (2011), 751-765.
Boutsidis, C., et al., "SVD based initialization: a head start for nonnegative matrix factorization", Pattern Recogn. 41, (2008), 1350-1362.
Brennecke, P., "Accounting for technical noise in single-cell RNA-seq experiments", Nat. Methods 10(11), (Nov. 2013), 1093-1095.
Brunet, J.-P., et al., "Metagenes and molecular pattern discovery using matrix factorization", Proc. Natl Acad. Sci. USA 101(12), (2014), 4164-4169.
Chen, J., "Mpath maps multi-branching single-cell trajectories revealing progenitor cell progression during development", Nat. Commun. 7, 11988, (2016).
Csardi, G., et al., "The igraph software package for complex network research", Interjournal, Complex Systems 1695, (2006), 1-9.
De Val, S., et al., "Combinatorial regulation of endothelial gene expression by ets and forkhead transcription factors", Cell 135, (2008), 1053-1064.
Deveale, B., et al., "Oct4 is required BE7.5 for proliferation in the primitive streak", PLoS Genet. 9, e1003957, (2013), 1-16.
Downs, K. M., et al., "Staging of gastrulating mouse embryos by morphological landmarks in the dissecting microscope", Development 118, (1993), 1255-1266.
Dumont, D. J., et al., "Dominant-negative and targeted null mutations in the endothelial receptor tyrosine kinase, tek, reveal a critical role in vasculogenesis of the embryo", Genes Dev. 8, (1994), 1897-1909.
Dyer, M. A., et al., "Indian hedgehog activates hematopoiesis and vasculogenesis and can respecify prospective neurectodermal cell fate in the mouse embryo", Development 128, (2001), 1717-1730.
Ferdous, A., et al., "Nkx2-5 transactivates the Ets-related protein 71 gene and specifies an endothelial/endocardial fate in the developing embryo", Proc. Natl. Acad. Sci. USA, 106(3), (2009), 814-819.

(Continued)

*Primary Examiner* — John S Brusca
(74) *Attorney, Agent, or Firm* — Schwegman Lundberg & Woessner, P.A.

(57) ABSTRACT

Developmental, stem cell and cancer biologists are interested in the molecular definition of cellular differentiation. Although single-cell RNA sequencing represents a transformational advance for global gene analyses, novel obstacles have emerged, including the computational management of dropout events, the reconstruction of biological pathways and the isolation of target cell populations. Provided herein is an algorithm named dpath that applies the concept of metagene entropy and allows the ranking of cells based on their differentiation potential. Also provided herein are self-organizing map (SOM) and random walk with restart (RWR) algorithms to separate the progenitors from the differentiated cells and reconstruct the lineage hierarchies in an unbiased manner. These algorithms were tested using single cells from Etv2-EYFP transgenic mouse embryos and reveal specific molecular pathways that direct differentiation programs involving the haemato-endothelial lineages. This software program quantitatively assesses the progenitor and committed states in single-cell RNA-seq data sets in a non-biased manner.

20 Claims, 10 Drawing Sheets
(6 of 10 Drawing Sheet(s) Filed in Color)

(56) References Cited

PUBLICATIONS

Grun, D., et al., "Validation of noise models for single-cell transcriptomics", Nat. Methods 11(6), (2014), 637-640.

Grün, D., et al., "De Novo Prediction of Stem Cell Identity using Single-Cell Transcriptome Data", Cell Stem Cell. 19(2), (2016), 266-277.

Haghverdi, L., et al., "Diffusion maps for high-dimensional single-cell analysis of differentiation data", Bioinformatics 31(18), (2015), 2989-2998.

Hart, A. H., et al., "Identification, Cloning and Expression Analysis of the Pluripotency Promoting Nanog Genes inMouse and Human", Developmental Dynamics, 230, (2004), 187-198.

Heinaniemi, M., et al., "Gene-pair expression signatures reveal lineage control", HHS Public Access, Author Manuscript, published in final edited form as: Nat Methods 10(6) (2013), 577-583, (2013), 19 pgs.

Kataoka, H., et al., "Expressions of PDGF receptor alpha, c-Kit and Flk1 genes clustering in mouse chromosome 5 define distinct subsets of nascent mesodermal cells", Dev. Growth Differ. 39(6), (1997), 729-740.

Kim, D. H., et al., "Single-cell transcriptome analysis reveals dynamic changes in lncRNA expression during reprogramming", Cell Stem Cell 16, (2015), 88-101.

Kim, P. G., et al., "Signaling axis involving Hedgehog, Notch, and Scl promotes the embryonic endothelial-to-hematopoietic transition", Proc. Natl Acad. Sci. USA 110, (2013), E141-E150.

Kohonen, T., "Table of Contents, Self-Organizing Maps", Springer Series in Information Sciences, (2001), 7 pgs.

Koyano-Nakagawa, Naoko, et al., "Etv2 is expressed in the yolk sac hematopoietic and endothelial progenitors and regulates Lmo2 gene expression", Stem Cells, 30(8), (2012), 1611-1623.

Lee, D., et al., "ER71 acts downstream of BMP, Notch, and Wnt signaling in blood and vessel progenitor specification", Cell Stem Cell 2, (2008), 497-507.

Lee, D. D., et al., "Learning the parts of objects by non-negative matrix factorization", Nature, 401, (1999), 10 pgs.

Li, G., et al., "Transcriptomic profiling maps anatomically patterned subpopulations among single embryonic cardiac cells", Dev. Cell 39(4), (2016), 491-507.

Li, Y., et al., "Genome-wide inferring gene-phenotype relationship by walking on the heterogeneous network", Bioinformatics 26, (2010), 1219-1224.

Liu, F., et al., "Induction of hematopoietic and endothelial cell program orchestrated by ETS transcription factor ER71/ETV2", EMBO Rep. 16, (2015), 654-669.

Lou, X., et al., "Smarcd3b and Gata5 promote a cardiac progenitor fate in the zebrafish embryo", Development 138, (2011), 3113-3123.

MacArthur, B. D., et al., "Statistical mechanics of pluripotency", Cell 154, (2013), 484-489.

Misfeldt, A. M., et al., "Endocardial cells are a distinct endothelial lineage derived from Flk1lo multipotent cardiovascular progenitors", Dev. Biol. 333, (2009), 78-89.

Ohnishi, Y., et al., "Cell-to-cell expression variability followed by signal reinforcement progressively segregates early mouse lineages", HHS Public Access, Author Manuscript, Published in final edited form as: Nat Cell Biol., 16(1), (2014), 27-37, (2014), 24 pgs.

Page, L., et al., "The PageRank Citation Ranking: Bringing Order to the Web", Stanford Digital Library Technologies Project, (Jan. 29, 1998), 1-17.

Palencia-Desai, S., et al., "Vascular endothelial and endocardial progenitors differentiate as cardiomyocytes in the absence of Etsrp/Etv2 function", Development 138, (2011), 4721-4732.

Pierre, M., et al., "VEGF and IHH Rescue Definitive Hematopoiesis in Gata-4 and Gata-6 Deficient Murine Embryoid Bodies", HIH Public Access, Author Manuscript, Published in final edited form as: Exp Hematol., 37(9), (2009), 1038-1053, (2009), 26 pgs.

Pierson, E., et al., "ZIFA: dimensionality reduction for zero-inflated single cell gene expression analysis", Genome Biol. 16: 241, (2015), 10 pgs.

Rasmussen, T. L., et al., "ER71 directs mesodermal fate decisions during embryogenesis", Development 138, (2011), 4801-4812.

Robb, L., et al., "Absence of yolk sac hematopoiesis from mice with a targeted disruption of the scl gene", Proc. Natl Acad. Sci. USA 92, (1995), 7075-7079.

Sato, T. N., et al., "Distinct roles of the receptor tyrosine kinases Tie-1 and Tie-2 in blood vessel formation", Nature 376, (1995), 70-74.

Scialdone, A., et al., "Resolving Early Mesoderm Diversification through Single Cell Expression Profiling", Europe PMC Finders Group, Author Manuscript, Published in final edited form as: Nature, 535(7611), (2016), 289-293, (2016), 40 pgs.

Setty, M., et al., "Wishbone identifies bifurcating developmental trajectories from single-cell data", HHS Public Access, Author Manuscript, Published in final edited form as: Nat Biotechnol., 34(6), (2016), 637-645, (2016), 37 pgs.

Shalaby, F., et al., "A requirement for Flk1 in primitive and definitive hematopoiesis and vasculogenesis", Cell, 89, (1997), 981-990.

Singh, B. N., et al., "Hedgehog Signaling during Appendage Development and Regeneratio", Genes (Basel) 6, (2015), 417-435.

Stainier, D. Y., et al., "cloche, an early acting zebrafish gene, is required by both the endothelial and hematopoietic lineages", Development 121, (1995), 3141-3150.

Subramanian, A., et al., "Gene set enrichment analysis: a knowledge-based approach for interpreting genome-wide expression profiles", Proc. Natl. Acad. Sci. USA, 102(43):, (2005), 15545-1550.

Takakura, N., et al., "Critical Role of the TIE2 Endothelial Cell Receptor in the Development of Definitive Hematopoiesis", Immunity 9, (1998), 677-686.

Tanaka, Y., et al., "Circulation-independent differentiation pathway from extraembryonic mesoderm toward hematopoietic stem cells via hemogenic angioblasts", Cell Rep. 8, (2014), 31-39.

Tang, F., et al., "Tracing the derivation of embryonic stem cells from the inner cell mass by single-cell RNA-Seq analysis", Cell Stem Cell 6, (2010), 468-478.

Tong, H. H., et al., "Random walk with restart: fast solutions and applications", Knowl. Inf. Syst. 14, (2008), 327-346.

Trapnell, C., et al., "Differential gene and transcript expression analysis of RNAseq experiments with TopHat and Cufflinks", Nat. Protoc. 7, (2012), 562-578.

Trapnell, C., et al., "Pseudo-temporal ordering of individual cells reveals dynamics and regulators of cell fate decisions", HHS Public Access, Author Manuscript, Published in final edited form as: Nat Biotechnol., 32(4) (2014), 381-386, (2014), 12 pgs.

Treutlein, B., et al., "Reconstructing lineage hierarchies of the distal lung epithelium using single-cell RNA-seq", HHS Public Access, Author Manuscript, Published in final edited form as: Nature, 509(7500), (2014), 371-375, (2014), 31 pgs.

Usoskin, D., et al., "Unbiased classification of sensory neuron types by large-scale single-cell RNA sequencing", Nat. Neurosci. 18, (2014), 1-11.

Van Der Maaten, L., et al., "Visualizing Data Using t-SNE", J. Mach. Learn. Res. 9, (2008), 2579-2605.

Visvader, J. E., et al., "Unsuspected role for the T-cell leukemia protein SCL/tal-1 in vascular development", Genes Dev., 12, (1998), 473-479.

Von Gise, A., et al., "Endocardial and epicardial epithelial to mesenchymal transitions in heart development and disease", Circ. Res. 110(12), (2012), 1628-1645.

Wang, G., et al., "LS-NMF: a modified non-negative matrix factorization algorithm utilizing uncertainty estimates", BMC Bioinformatics 7: 175, (2016), 10 pgs.

Wehrens, R., et al., "Self- and super-organizing maps in R: the Kohonen package", J. Stat. Softw. 21, (2007), 1-19.

Zeisel, A., et al., "Cell types in the mouse cortex and hippocampus revealed by single-cell RNA-seq.", Science 347, (2015), 1138-1142.

\* cited by examiner

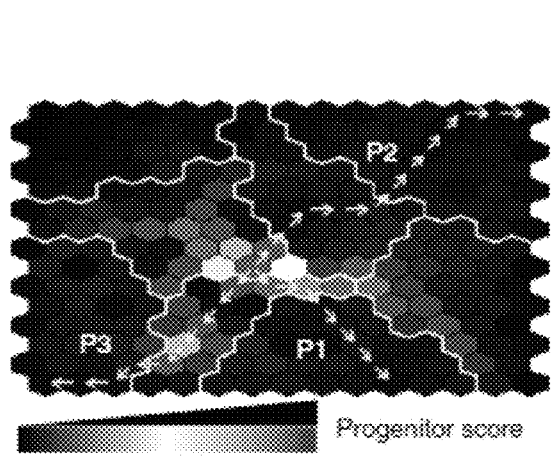
FIG. 5A
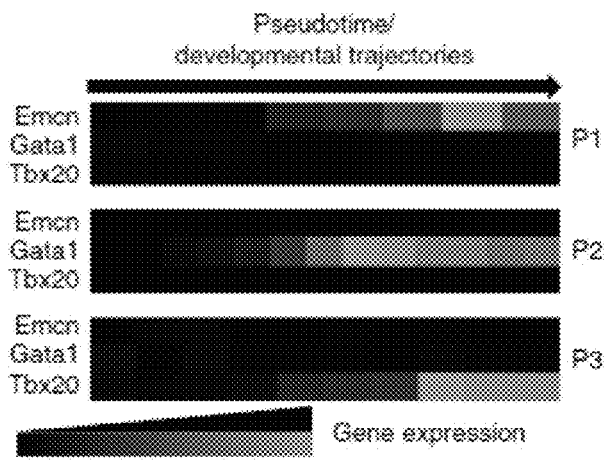
FIG. 5B
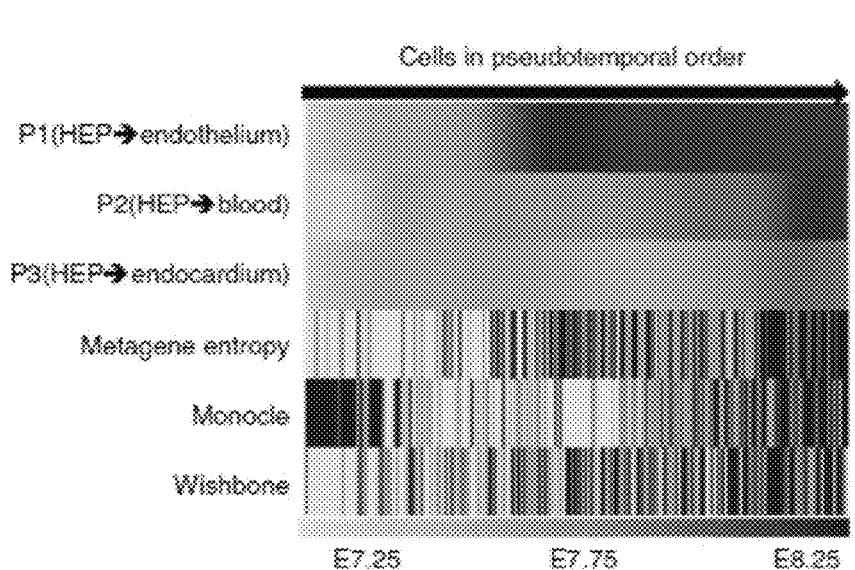
FIG. 5C
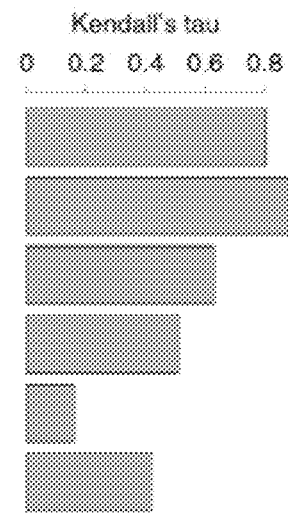

ANALYSIS OF SINGLE CELL TRANSCRIPTOMICS

PRIORITY

This application claims the benefit of priority from U.S. Provisional Patent Application Ser. No. 62/309,861, filed on Mar. 17, 2016, which is herein incorporated in its entirety by reference.

BACKGROUND

Developmental, stem cell and cancer biologists are interested in the molecular definition of cellular differentiation. While single cell RNA sequencing represents a transformational advance for global gene analyses, novel obstacles have emerged, including the computational management of dropout events, the reconstruction of biological pathways, and the isolation of target cell populations.

Cardiovascular lineages, including: blood, endothelium, endocardium, and myocardium, arise within a narrow time window from nascent mesoderm exiting the primitive streak and these lineages develop in synchrony to form the circulatory system. The haematopoietic and the endothelial lineages are closely related and express a number of common transcripts (1). Based on the number of gene mutations that affect both haematopoietic and endothelial lineages, it has been proposed that that they arise from common progenitors (2-10). The bifurcation point of these two lineages in embryos, however, has been debated and the gene expression profiles of the progenitors have not been fully defined, in part, due to the difficulty with the isolation of these bipotential cell populations.

SUMMARY

The molecular definition of differentiation is of intense interest for developmental and stem cell biologists. While single cell RNA sequencing represents a transformational advance for global gene analyses, certain obstacles have emerged including: the computational management of dropout events, the reconstruction of biological pathways and the isolation of target cell populations. Described herein is the use of Etv2-EYFP transgenic embryos to isolate hematopoietic, endothelial and endocardial progenitors and perform single cell transcriptome analyses. The analyses revealed specific molecular and signaling pathways that directed differentiation programs of the hematopoietic and endothelial lineages. A concept of metagene entropy is discussed, that enables one to rank cells based on their differentiation potential. An example of analysis software according to one embodiment is referred to herein as 'dpath' and can be configured as a downloadable package. This is the first software program that quantitatively assesses the progenitor and committed states in single cell RNA-seq datasets and will be a powerful tool for stem cell biologists. Among other things, quantitative single-cell RNA-seq can be used, for example, to perform a molecular census of the primary somatosensory cortex (Si) and the hippocampal CA1 region, based on greater than 3,005 single-cell transcriptomes.

One embodiment provides a machine readable medium with instructions for analyzing cellular differentiation, the instructions, when executed by processing circuitry, cause the processing circuitry to perform operations comprising: receiving an expression profile matrix for a single cell RNA-seq dataset; decomposing the expression profile matrix; quantitatively assessing the cellular state; and prioritizing genes for progenitor and committed cellular states. In one embodiment, decomposing the expression profile matrix includes identifying metagenes using weighted Poisson non-negative matrix factorization. In another embodiment, the machine readable medium of claim 1, wherein an expected gene expression level is modeled as a linear combination of non-negative metagene basis and coefficients. In one embodiment, an observed gene expression level is modeled as a mixture of Poisson distribution of expected expression level and a dropout event represented by a low-magnitude Poisson process. In another embodiment, decomposing the expression matrix includes approximating a product of non-negative metagene basis and coefficients. In one embodiment, the metagene basis corresponds to a contribution of each gene to each metagene. In another embodiment, the metagene coefficient corresponds to a probabilistic simplex that indicates the relative weight of each metagene in each cell.

In one embodiment, the machine readable medium further includes assigning a metagene signature for an individual cell. In another embodiment, the machine readable medium of further includes mapping cells into metacells using a self-organizing map (SOM). In another embodiment the machine readable medium further including ranking cells with respect to specific cellular states including: generating a heterogeneous metagene-metacell graph; and using a random walk with restart process on the heterogeneous metagene-metacell graph. In one embodiment, the machine readable medium further including ranking genes for cellular states according to their expression profile. In another embodiment prioritizing genes for progenitor and committed cellular states includes determining a measure of metagene entropy for cells. In one embodiment, the machine readable medium further including imposing a requirement in which the metagene expression profiles between cells in neighboring development stages are similar. In one embodiment, the machine readable medium includes using a self-organized map. In one embodiment, using the self-organized map includes correlating a hexagonal grid of the map with a cell expression pattern. In another embodiment, the machine readable medium further including clustering cells by partitioning the map. In one embodiment, a central cell of the map is correlated with an early progenitor. In one embodiment, a peripheral cell of the map is correlated with a mature cell. In another embodiment, prioritizing genes for progenitor and committed cellular states includes generating a transition matrix. In one embodiment, the machine readable medium includes classifying a metacell as a progenitor of a neighboring metacell if the metagene entropy is higher than a derivative metacell.

In one embodiment, the machine readable medium includes using a random walk with restart (RWR) process on the heterogeneous graph to determine a probability of a metacell being in a committed state to one metagene, or being in a progenitor state with the ability to transition to multiple metagenes. In one embodiment, the machine readable medium includes identifying a developmental trajectory based on a path length of the self-organized map.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5. dpath allows the definition of the developmental trajectory and hierarchy of lineages. (a) The developmental trajectories were indicated from the high entropy progenitor (HEP) cellular state toward the committed cellular states of endothelium, blood and endocardium. The most likely progenitor cellular state and committed cellular states were determined by a RWR algorithms on a metagene-metacell heterogeneous graph. The developmental trajectories between the progenitor and committed cellular states were determined as the shortest paths (between the progenitor and the committed/differentiated cell) on the metacell landscape. P1, P2 and P3 represented the predicted developmental trajectories toward committed endothelial, committed haematopoietic and committed endocardial lineages. (b) The heatmaps show the expression pattern of Emcn, Gata1 and Tbx20 along the trajectories P1, P2 and P3. (c) The Kendall rank correlation coefficients between the pseudotime and temporal labels (E7.25, E7.75 and E8.25) were used to evaluate the performance of trajectory inference. For dpath, the lineage-specific cells were ordered into pseudotemporal order along three separate trajectories P1, P2 and P3, respectively. The cells were also reordered merely based on their metagene entropy. For Monocle and Wishbone, we used the cell-wise pseudotime reported by the algorithms.

DETAILED DESCRIPTION

Definitions

Figure 1A:
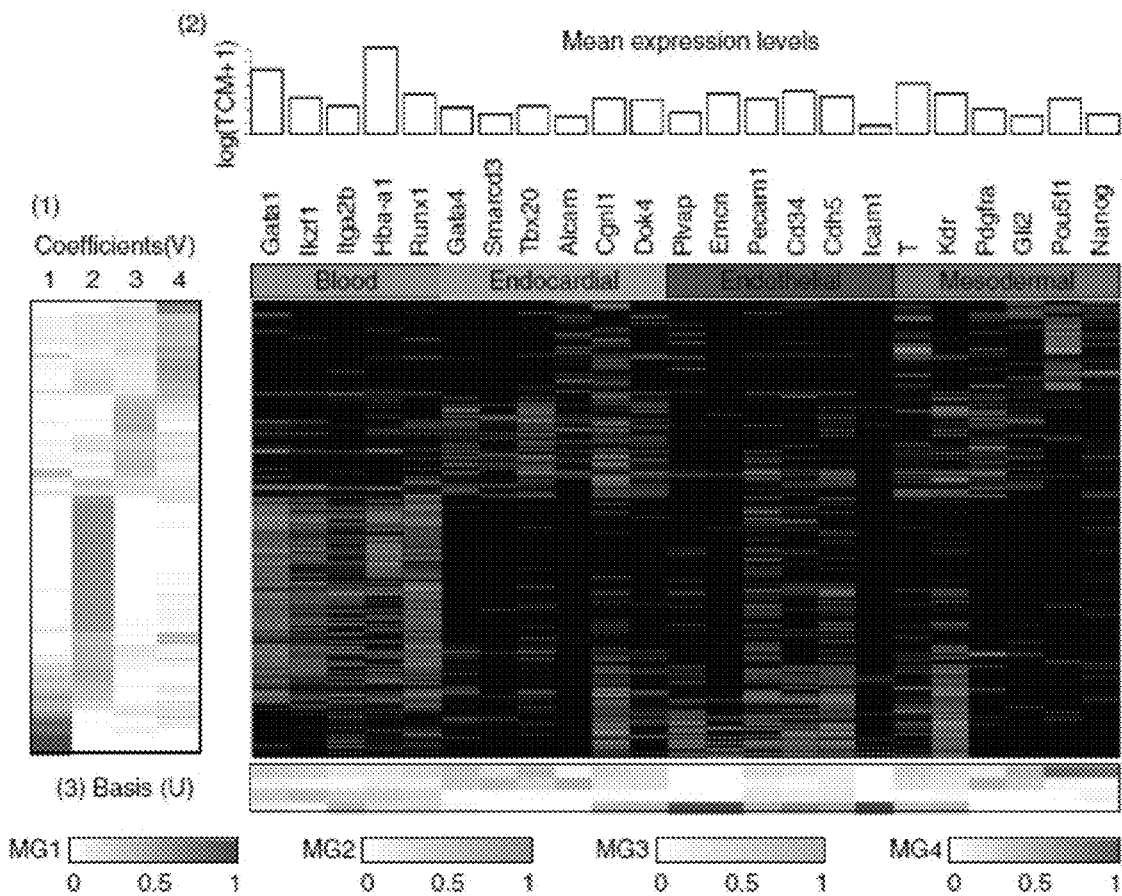
FIG. 1. dpath successfully separated Etv2-EYFP$^+$ cells into four metagenes. (a) Wp-NMF decomposed the expression profile matrix of Etv2-EYFP$^+$ cells into metagene coefficients and metagene basis. Selected markers of expected lineages were used to identify the lineage represented by each metagene. (1) The heatmap showed the cell-wise metagene coefficients. Every row represented a single cell and the colour indicated the expression intensity of metagenes in each cell (cell-wise metagene signature). (2) Bar plot indicated the median expression levels of a list of known marker genes for haematopoietic, endocardial and endothelial lineages and the mesodermal progenitors across all 291 single cells. The heatmap showed each gene's observed cell-wise expression levels, scaled to a minimum of zero (black) and a maximum of one (green). (3) The heatmap showed the metagene basis for selected marker genes. Every column represented a gene and the colour indicated the contribution of each gene to each metagene. (b-e) GSEA showed that genes ranked by the correlation between their expression levels and cell-wise metagene coefficients of four metagenes were significantly associated with distinct Gene Ontology terms (*$0.01 \leq P$ value<0.05; $0.001 \leq P$ value<0.01; *P value<0.001. The statistical significance (nominal P value) was estimated by the permutation test. In each panel, x axis indicated the genes ordered according to the correlation between their expression levels and cell wise metagene coefficients, and y axis indicated the ES score from the GSEA.
Figure 1B:
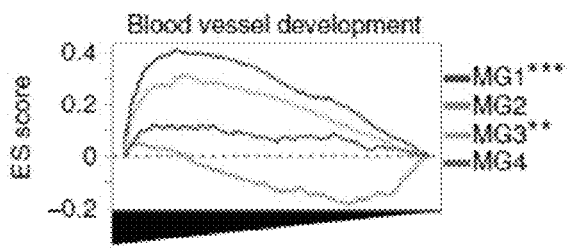
Figure 1C:
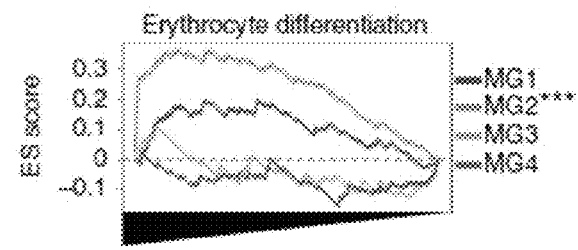
Figure 1D:
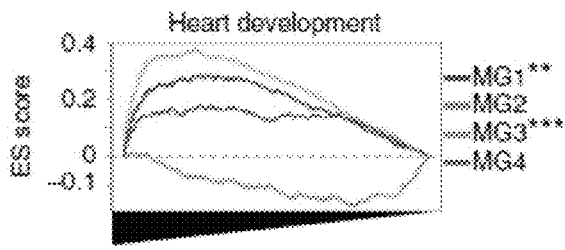
Figure 1E:
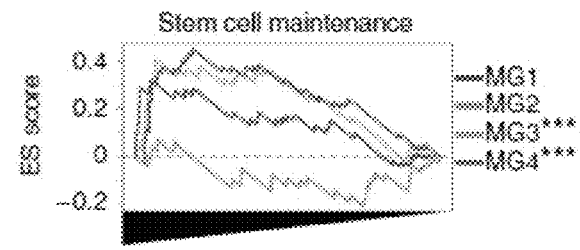

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Any methods and materials similar or equivalent to those described herein can be used in the practice or testing of the present invention. Specific and preferred values listed below for radicals, substituents, and ranges are for illustration only; they do not exclude other defined values or other values within defined ranges for the radicals and substituents.

As used herein, the articles "a" and "an" refer to one or to more than one, i.e., to at least one, of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

"Cells" include cells from, or the "subject" is, a vertebrate, such as a mammal, including a human. Mammals include, but are not limited to, humans, farm animals, sport animals and companion animals. Included in the term "animal" is dog, cat, fish, gerbil, guinea pig, hamster, horse, rabbit, swine, mouse, monkey (e.g., ape, gorilla, chimpanzee, or orangutan), rat, sheep, goat, cow and bird.

Totipotent (a.k.a. omnipotent) stem cells can differentiate into embryonic and extraembryonic cell types. Such cells can construct a complete, viable organism. These cells are produced from the fusion of an egg and sperm cell. Cells produced by the first few divisions of the fertilized egg are also totipotent. Pluripotent stem cells are the descendants of totipotent cells and can differentiate into nearly all cells, i.e. cells derived from any of the three germ layers. Multipotent stem cells can differentiate into a number of cell types, but only those of a closely related family of cells. Oligopotent stem cells can differentiate into only a few cell types, such as lymphoid or myeloid stem cells. Unipotent cells can produce only one cell type, their own,[4] but have the property of self-renewal, which distinguishes them from non-stem cells (e.g. progenitor cells, muscle stem cells).

"Progenitor cells" are cells produced during differentiation of a stem cell that have some, but not all, of the characteristics of their terminally differentiated progeny. Defined progenitor cells, such as "endothelial progenitor cells," are committed to a lineage, but not to a specific or terminally differentiated cell type.

"Self-renewal" refers to the ability to produce replicate daughter stem cells having differentiation potential that is identical to those from which they arose. A similar term used in this context is "proliferation."

"Expansion" refers to the propagation of a cell or cells without differentiation.

The terms "comprises," "comprising," and the like can have the meaning ascribed to them in U.S. Patent Law and can mean "includes," "including" and the like. As used herein, "including" or "includes" or the like means including, without limitation.

ASPECTS OF THE INVENTION

Etv2, an ETS domain transcription factor, plays a role endothelial, endocardial and haematopoietic development and has a negative impact on myocardial development (11-15). Etv2 mutants are nonviable and completely lack haematopoietic and endothelial lineages. Furthermore, Etv2 overexpression in differentiating embryonic stem cells (ESs) induces the haematopoietic and endothelial lineages (13, 16). Etv2 is expressed in a narrow developmental window starting from embryonic day 7 (E7.0) and has diminished expression after E8.5 during murine embryogenesis (14, 16). Collectively, these data support a role for Etv2 in mesodermal differentiation at the junction of blood, endothelial and cardiac lineages. In the present study, Etv2-EYFP transgenic embryos (14) and single-cell RNA-seq analysis was used to develop a blueprint of the lineage hierarchies of Etv2-positive cells early during development.

Single-cell RNA-seq provides an unprecedented opportunity to study the global transcriptional dynamics at the single-cell resolution (17-23). Although multiple methods have been published to analyze the single-cell sequencing data, there are technical hurdles that need to be resolved in order to fully appreciate the biological impact. Herein is described mathematical solutions to two major issues encountered by the single-cell RNA-seq field. The first issue addresses the dropout events, arising from the systematic noise. This is a common problem in which an expressed gene observed in one cell cannot always be detected in another cell from the same population (24). The presence of dropout events combined with sampling noise and the natural stochasticity and diversity of transcriptional regulation at the single-cell level (25) makes profiling the low amounts of mRNA within individual cells extremely challenging. Herein is provided a weighted Poisson non-negative matrix factorization (wp-NMF) method as a solution to this problem.

The second outstanding issue is the need for additional biological information to determine the directionality of differentiation using the currently available methods. A number of conventional methods allow one to cluster cells into subpopulations and qualitatively associate the subpopulations with different cellular states during embryogenesis (19). Recently, several single cell RNA-seq analysis pipelines were developed to detect the branching trajectories and order single cells based on their maturity (23, 26-28). However, these methods required either a set of differentially expressed genes be predefined or the beginning and the end of the trajectory be determined by the investigator, limiting their general and non-biased applicability to a heterogeneous novel cell population. Herein is described a concept termed metagene entropy, which is combined with a self-organizing map (SOM) and random walk with restart (RWR) algorithms to separate the progenitors from the differentiated cells and reconstruct the lineage hierarchies in an unbiased fashion. In these studies, solutions to these two major issues are provided in the analysis of single-cell RNA-seq data. An R package was developed named dpath that decomposes the expression profiles with the awareness of the dropout events, quantitatively assesses the cellular state and prioritizes genes for both progenitor and committed cellular states. A head-to head comparison was undertaken with commonly used factorization methods and pseudotime inference algorithms and demonstrate the superiority of the dpath program. Finally, dpath was used to decipher three major lineages of Etv2$^+$ cells and identify key genes and signalling pathways for the group of progenitor cells with both endothelial and haematopoietic characteristics. This program, dpath, will facilitate and decipher the biological mechanisms that govern stem cell and progenitor cell populations.

Figure 6:
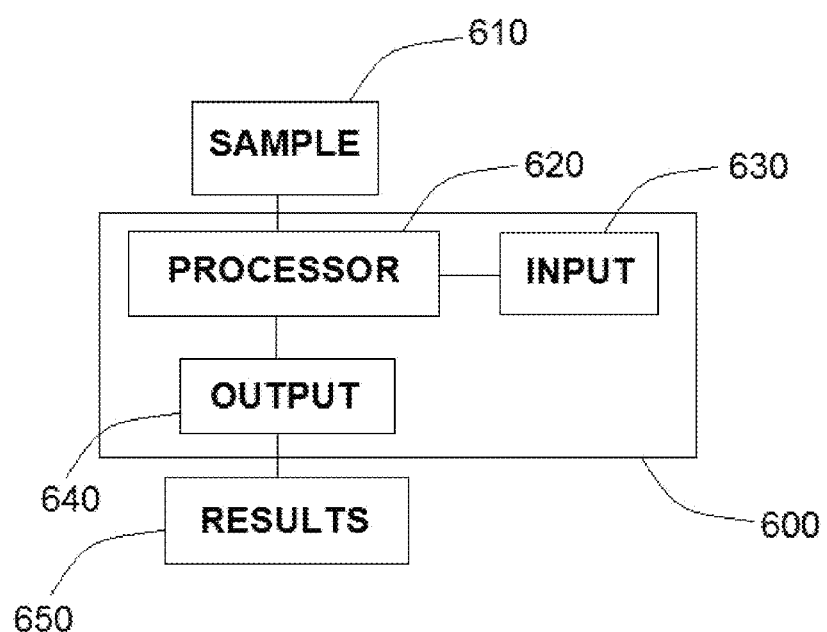
FIG. 6 illustrates a block diagram of a system, in accordance with one example of the present subject matter.

FIG. 6 illustrates a block diagram of system 600, in accordance with one example of the present subject matter. System 600 includes processor 620, input 630, and output 640. Processor 620 can include a DNA/RNA sequencing machine. In various examples, processor 620 can be configured to filter, amplify, react, or analyse a specimen. Processor 620 can evaluate metagene entropy, allow ranking of cells, generate a self-organized map, conduct random walk with restart analysis, separate progenitors from differentiated cells, reconstruct lineage, identify pathways, quantitatively assess progenitor, and committed states in data sets. Input 630 can include user controls or a user interface to allow an operator to manage operation of processor 620. Input 630 can include a keyboard, a user module, a cursor control, or other user-operable interface. Output 640 can include an output device such as a printer, a display, an interface, or a telemetry module. Output 640 can render the output from processor 620.

As illustrated, system 600 can be configured to receive sample 610 and provide result 650. Sample 610 can include an embryo. Result 650 can include a determination as to gene analysis including data as to a biological pathway or an isolated target cell population.

Figure 7:
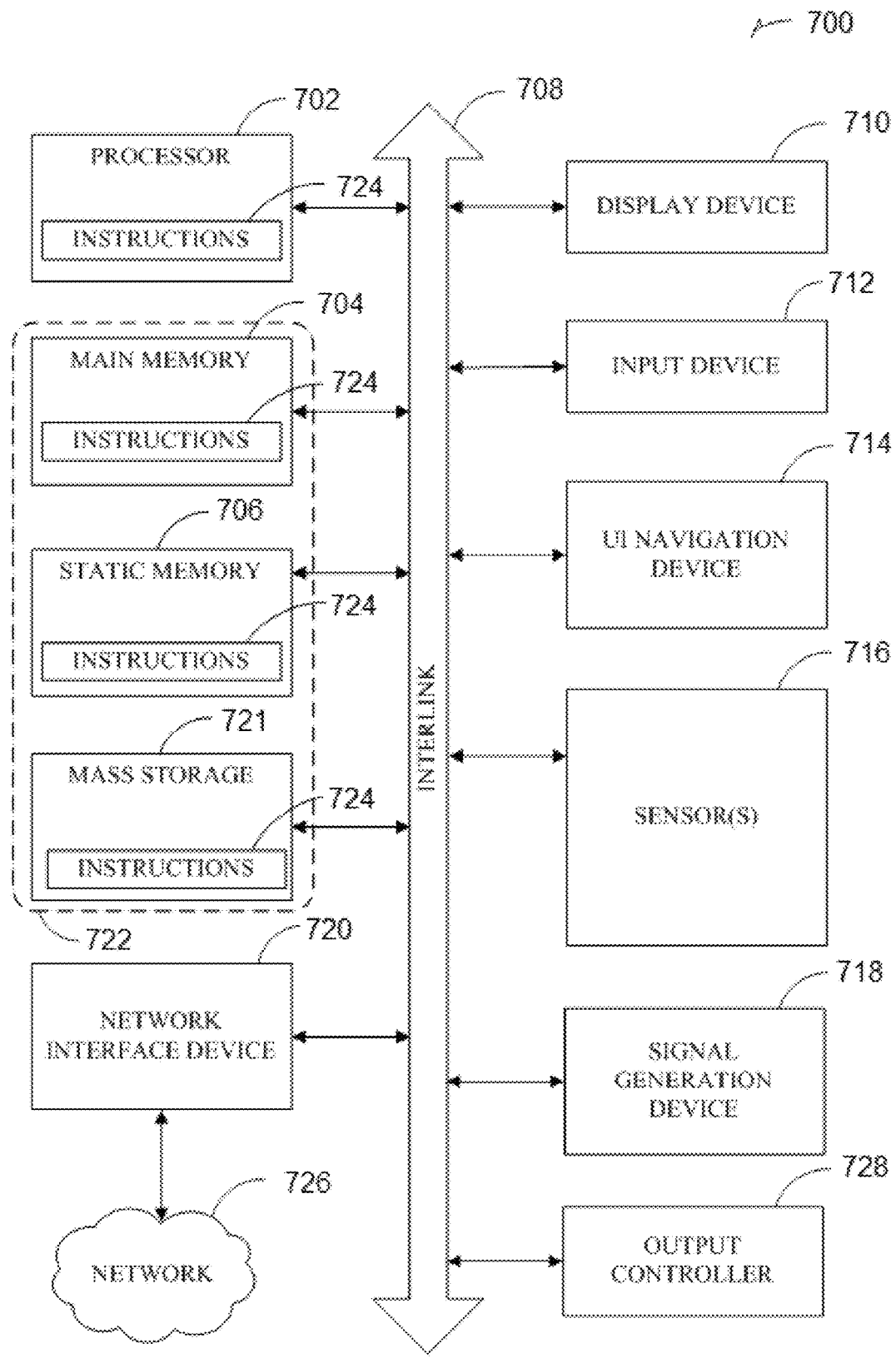
FIG. 7 illustrates a block diagram of a system, in accordance with one example of the present subject matter.

FIG. 7 illustrates a block diagram of an example machine 700 upon which any one or more of the techniques (e.g., methodologies) discussed herein may perform. Examples, as described herein, may include, or may operate by, logic or a number of components, or mechanisms in the machine 700. Circuitry (e.g., processing circuitry) is a collection of circuits implemented in tangible entities of the machine 700 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 700 follow.

In one embodiment, the machine 700 may operate as a standalone device or may be connected (e.g., networked) to other machines. An example of another machines can include a sequencer. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 700 may include a hardware processor 702 (e.g., a central processing unit (CPU), a graphics processing unit (GPU), a hardware processor core, or any combination thereof), a main memory 704, a static memory (e.g., memory or storage for firmware, microcode, a basic-input-output (BIOS), unified extensible firmware interface (UEFI), etc.) 706, and mass storage 721 (e.g., hard drive, tape drive, flash storage, or other block devices) some or all of which may communicate with each other via an interlink (e.g., bus) 708. The machine 700 may further include a display unit 710, an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 702, the main memory 704, the static memory 706, or the mass storage 716 may be, or include, a machine readable medium 722 on which is stored one or more sets of data structures or instructions 724 (e.g., software) embodying or utilized by any one or more of the techniques or functions described herein. The instructions 724 may also reside, completely or at least partially, within any of registers of the processor 702, the main memory 704, the static memory 706, or the mass storage 716 during execution thereof by the machine 700. In an example, one or any combination of the hardware processor 702, the main memory 704, the static memory 706, or the mass storage 716 may constitute the machine readable media 702. While the machine readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine readable medium examples may include solid-state memories, optical media, magnetic media, and signals (e.g., radio frequency signals, other photon based signals, sound signals, etc.). In an example, a non-transitory machine readable medium comprises a machine readable medium with a plurality of particles having invariant (e.g., rest) mass, and thus are compositions of matter. Accordingly, non-transitory machine-readable media are machine readable media that do not include transitory propagating signals. Specific examples of non-transitory machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may be further transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software. A transmission medium is a machine readable medium.

Figure 8:
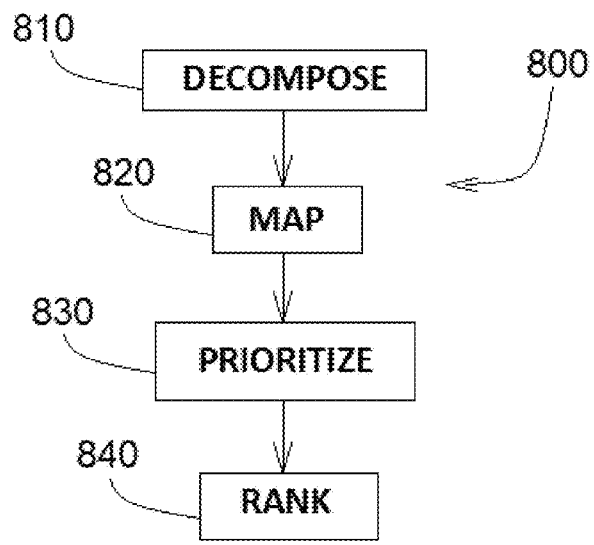
FIG. 8 illustrates a flow chart of a method, in accordance with one example of the present subject matter.

FIG. 8 illustrates a flow chart of method 800, in accordance with one example of the present subject matter. Method 800, in one example, is configured to perform single-cell RNA-seq analysis using the dpath pipeline. Method 800 can include, at 810, decomposing the expression profile matrix of single-cell RNA-seq into metagenes using wp-NMF. At 820, method 800 include mapping cells into metacells using a SOM algorithm. At 830, method 800 includes prioritizing cells with respect to specific cellular states using a RWR algorithm on a heterogeneous metagene-metacell graph. At 840, method 800 can include ranking genes for cellular states according to their expression profile. Method 800 can include addition or different elements as well.

Figure 9:
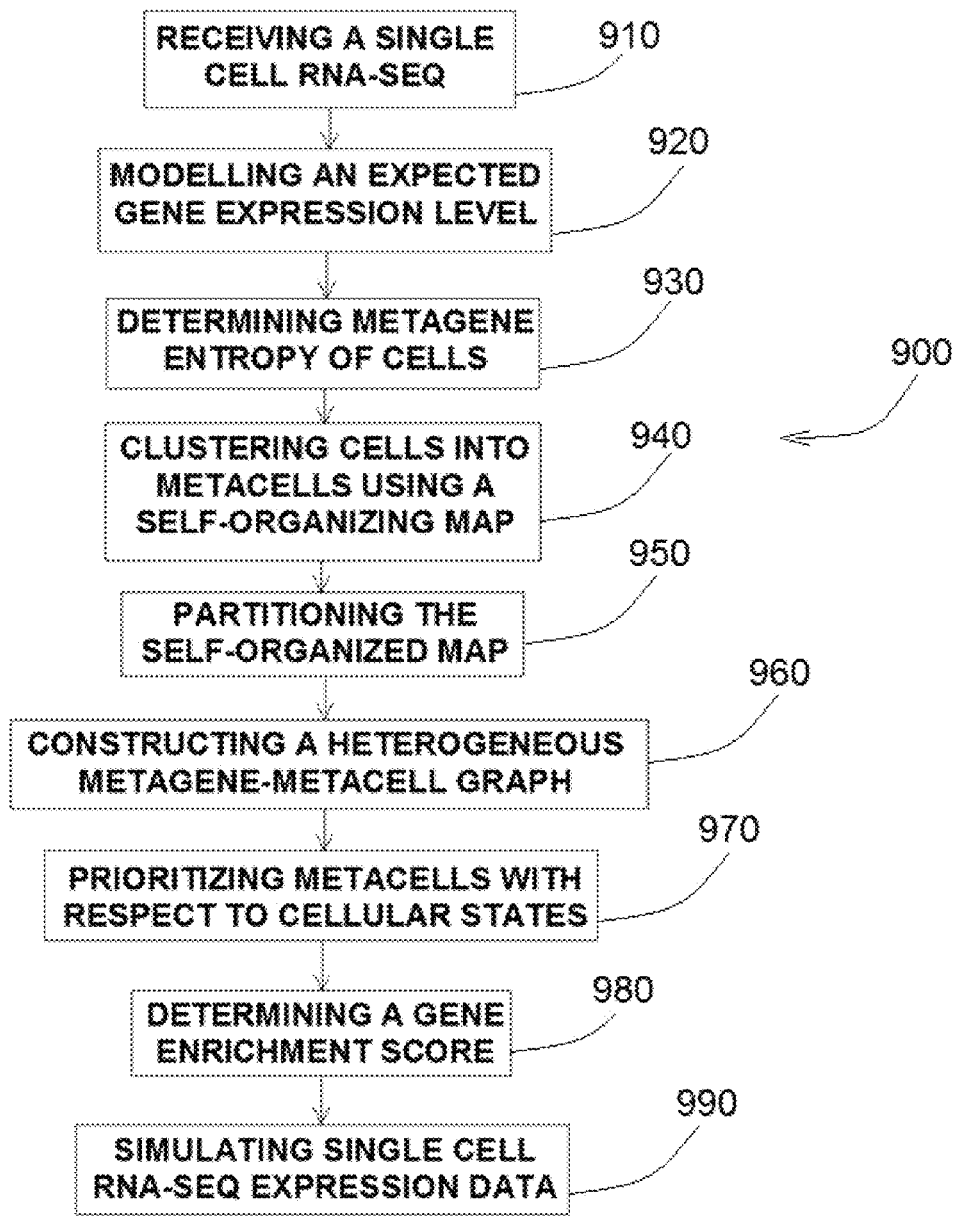
FIG. 9 illustrates a flow chart of a method, in accordance with one example of the present subject matter.

FIG. 9 illustrates a flow chart of method 900, in accordance with one example of the present subject matter. At 910, method 900 includes receiving a single cell RNA-seq. At 920, method 900 includes modelling an expected gene expression level. The expected gene expression level can be modelled as the linear combination of non-negative metagene basis and coefficients. The observed gene expression level can be modelled as a mixture of Poisson distribution of expected expression level and a dropout event represented by a low-magnitude Poisson process. At 930, method 900 includes determining metagene entropy. Metagene entropy can be determined by non-negative singular value decomposition. At 940, method 900 includes clustering cells into metacells using a self-organized map. The map can be organized on a two dimensional hexagonal grid. At 950, method 900 includes partitioning the self-organized map using partitioning around medoids. Partitioning can include connected clusters. At 960, method 900 includes constructing a heterogeneous metagene-metacell graph. This can include determining a transition probability matrix. At 970, method 900 can include prioritizing metacells with respect to cellular states (committed or progenitor). In one example, a random walk with restart algorithm can be executed to prioritize metacells. In one example, the user can specific a parameter β associated with the probability of staying in the metagene graph. At 980, method 900 includes determining a gene enrichment score. The enrichment score is based on the sum of steady state probabilities. At 990, method 900 includes simulating a single cell RNA-seq expression data.

The following example is intended to further illustrate certain embodiments and is not intended to limit the scope in any way.

EXAMPLE

Dpath Software Reveals Hierarchical Haemato-Endothelial Lineages of Etv2 Progenitors Based on Single-Cell Transcriptome Analysis Materials and Methods Cell Isolation Cell isolation. Etv2-EYFP embryos were harvested from time mated females at E7.25, E7.75 or E8.25 and screened using microscopy for EYFP expression (14). Embryos were divided into EYFP-positive and -negative pools for dissociation with TrypLE Express (Gibco by Life Technologies). After dissociation, cells were diluted with 10% foetal bovine serum in DMEM and pelleted at 1,000 g. Cells were resuspended in 0.1% propidium iodide and 2% serum in PBS. EYFP-negative embryos were used as a gating control sample. Propidium iodide-negative, EYFP-positive cells were sorted by FACS using a MoFlo XDP (Beckman Coulter) into DMEM plus 10% foetal bovine serum. FACS sorted cells were resuspended at 500 cells $ul^{-1}$ before loading onto a Fluidigm 10-17 um integrated fluidics circuit for capture, viability screening, lysis and library amplification on a C1 Single-Cell Auto Prep System (Fluidigm).

Single-Cell RNA-Seq.

Libraries were analyzed for cDNA content by pico green staining. Wells that contained a single viable cell and at least 0.2 ng $ul^{-1}$ cDNA were chosen to proceed with sequencing. All libraries were sequenced using 75-bp paired end sequencing on a MiSeq (Illuminia), generating 202K-1, 910K paired end reads for each cell. The cells with <100K paired reads were removed, resulting in 281 cells for analysis. The transcripts per million (TPM) estimates were obtained with TopHat (v2.0.13) and Cufflinks (v2.2.1)61. The median mapping rate was 88.3%. Among 14,480 genes that could be detected in at least two cells (TPMZ1), a noise model was fitted with respect to each gene's mean and coefficient of variance (CV, s.d. divided by the mean) as $\log_2$ CV=$\log_2$ (mean$^\alpha$=k). Then 1,448 genes were removed with high technical noise, which were furthest from the fitted line (62,63). 7,240 ubiquitously expressed genes whose CV was below the median CV were also removed. The resulting 5,799 genes were used for the following analysis.

Weighted Poisson non-negative matrix factorization.

Let $X_{nm}$ be the log-transformed TPM of gene n in cell m. It was hypothesized that the expected log-transformed TPM of gene n in cell m, $u_{nm}$, could be represented as:

$$\mu_{nm} = \sum_{k=1}^{K} U_{nk} V_{km}$$

$$U_{nk} \geq 0, V_{km} \geq 0$$

$$\sum_{k=1}^{K} V_{km} = 1$$

where K was the number of metagenes, $U_{nk}$ was the metagene basis indicating the contribution of gene n on the kth metagene and $V_{km}$ was the metagene coefficient indicating the expression profile of the kth metagene in cell m. Specifically, the expected gene expression level was modelled as the linear combination of non-negative metagene basis and coefficients. The cell-wise metagene coefficients were summed up to one.

Similar to work by Kharchenko et al. (24) on the identification of differentially expressed genes in single-cell RNA-seq data, a weighted log-likelihood function for an observed expression level of gene n in cell m was defined as:

$$L_{\{U_n, V_m, \pi_{nm}\}} = \pi_{nm} \ln Pois(X_{nm}|\mu_{nm}) + (1-\pi_{nm}) \ln Pois(X_{nm}|\lambda_0)$$

where $\pi_{nm}$ ranges from zero to one, approximating the likelihood of gene n being expressed in cell m, that is, the probability that observed expression level $X_{nm}$ follows a Poisson distribution with the mean as $u_{nm}$. The dropout event was also modelled as a Poisson distribution with the mean as $\lambda_0$=0.1. As it was reasonable to hypothesize that $\pi_{nm}$ was proportional to the probability of being expressed, it could be estimated by:

$$\pi_{nm} = \frac{Pois(X_{nm}|\mu_{nm})}{Pois(X_{nm}|\mu_{nm}) + Pois(X_{nm}|\lambda_0)}$$

$\pi_{nm}$ could be viewed as a weight for the observed expression level of gene n in cell m, depending on the probability of being expressed over that of a dropout event.

Taken together, to decompose expression matrix into metagene basis and coefficients, such a constrained maximization problem was solved as:

$$\max_{U,V,\pi} \sum_{n=1}^{N} \sum_{m=1}^{M} L_{\{U_n, V_m, \pi_{nm}\}}$$

s.t. $\mu_{nm} = \sum_{k=1}^{K} U_{nk} V_{km}, \forall n = 1, \ldots, N; m = 1, \ldots, M$ $U_{nk} \geq 0, V_{km} \geq 0, \forall n = 1, \ldots, N; m = 1, \ldots,$ $M; k = 1, \ldots, K \sum_{k=1}^{K} V_{km} = 1, m = 1, \ldots, M$ Similar to solving a regular NMF problem with cost functions as Euclidean distance or Kullback-Leibler divergence, the objective function was optimized using a gradient ascent method and multiplicative rules to iteratively update U and V, until convergence or maximum iterations were reached:

$$\begin{cases} U \leftarrow U \circ \frac{[\pi \circ (X/UV)]V^T}{\pi V^T} \\ V \leftarrow V \circ \frac{U^T[\pi \circ (X/UV)]}{U^T \pi} \\ V \leftarrow V \text{diag}\left(1/\sum_{k=1}^{K} V_{k1}, \ldots, 1/\sum_{k=1}^{K} V_{kM}\right) \\ \pi_{nm} \leftarrow \frac{Pois(X_{nm}|\mu_{nm})}{Pois(X_{nm}|\mu_{nm}) + Pois(X_{nm}|\lambda_0)} \forall n = 1, \ldots, N; m = 1, \ldots, M \end{cases}$$

where '∘' was the Hadamard matrix product, '/' was the element-wise division and 'diag( . . . )' represents a diagonal matrix where diagonal entries are indicated by ' . . . '.

To accelerate the convergence, weighted NMF was used as a burn-in phase to initialize U and V, where a fixed weight of $w_0$=0.1 was given to the zero entries in the gene expression matrix X and a weight of one to non-zero entries (64). In weighted NMF, V was initialized using non-negative singular value decomposition (65).

The metagene entropy of cell m was defined as $$-\sum_{k=1}^{K} V_{km} \ln V_{km}$$

Choice of the size of metagene K.

As the objective function was not convex, wp-NMF may or may not converge to the same solution on each run, depending on the initialization of U. The wp-NMF was repeated for $r_{mf}$ times with different random initialization of U. The consensus matrix C and the cophenetic correlation coefficients pk (C) were computed as described in Brunet et al. (31). Values of K=4 were selected where the magnitude of the cophenetic correlation coefficient began to fall. The experiments also suggested that $r_{mf}$=20 was sufficient to obtain stable aggregated metagene coefficients, as the cophenetic correlation coefficients were not significantly less than $r_{mf}$=50 or 75.

Evaluating the performance of factorization methods.

For LOO-CV-based evaluation, we trained linear support vector machine classifiers were trained by using the factors from (m–1) cells and predicted the cell group (Emcn$^+$/Gata1$^-$/Tbx20$^-$, Gata1/Emcn$^-$/Gata1$^+$/Tbx20$^-$ and Emcn$^-$/Gata1$^-$/Tbx20$^+$) of the remaining cell. This procedure was repeated for every single cell and the LOO-CV error was determined as the overall prediction error. Lower LOO-CV error suggested better factorizations on capturing the difference of the three groups of cells. For WSS/TSS ratio-based evaluation, we computed the ratio of WSS and TSS of resulting factors. Lower WSS/TSS ratio suggested that three group of cells were more tightly clustered together on the reduced dimensions.

Clustering cells into metacells using a SOM.

SOM was used to map cells into P=225 prototype metacells that were spatially organized on a 15×15 2D hexagonal grid 44. The input space for SOM was the mean metagene expression profiles (metagene coefficients) V from $r_{mf}$ repetitive runs of wp-NMF. The R package kohonen was used to fit the SOM model with default parameters (66). $W_{kp}$ was used to represent scaled expression level of kth metagene in metacell p, where $$\Sigma_{k=1}^{K} W_{kp} = 1$$

Partitioning SOM using PAM.

The SOM were partitioned into multiple segments using PAM algorithm. If the number of desired clusters C was specified, the metacells were directly clustered into C clusters; otherwise, the SOM would be partitioned into the maximum number of clusters, as long as the size of each metacell cluster was no <15 and every metacell cluster was connected on the SOM (that is, no clusters were divided into two or more isolated regions).

Constructing a heterogeneous metagene-metacell graph.

A transition probability matrix was used to characterize the hierarchical relationships among P metacells and between P metacells and K metagenes. The transition probability matrix was defined as:

$$G = \begin{bmatrix} G_{MC} & G_{MCMG} \\ G_{MGMC} & \beta I \end{bmatrix}$$

where $\beta \in \{0,1\}$ and I was a K×K identity matrix.

As with the metagene entropy for the cells, we defined the metagene entropy of metacell p as:

$$H_p = -\sum_{k=1}^{K} W_{kp} \ln W_{kp}.$$

Based on the hypothesis that cells in a progenitor state have higher metagene entropy than cells at the committed state, we initially constructed a P×P directed metacell graph $G_{MC}$ for the hierarchical relationship of metacells. To prioritize committed (progenitor) states, for any metacell p on the SOM, the parental metacells were its neighbouring metacells in which metagene entropy was higher (smaller) than Hp and the derivative metacells were the neighbouring metacells where the metagene entropy was lower (higher) than Hp.

Thus the similarity between any two metacell p and q could be computed as:

$$A_{pq} = \begin{cases} 1/(1 + \|W_p - W_q\|_2, \\ 0, \end{cases}$$

if p was a parental metacell of q otherwise
where $\|W_p - W_q\|_2$ was the Euclidean distance between the metagene coefficients of metacell p and q.

Finally, the transition probability from metacell p to metacell q, from metagene k to metacell p and from metacell p to metagene k were defined as:

$$(G_{MC})_{pq} = \beta A_{pq} / \sum_{j=1}^{P} A_{pj}$$

$$(G_{MGMC})_{kp} = (1-\beta) W_{kp} / \sum_{i=1}^{P} W_{ki}$$

$$(G_{MCMG})_{pk} = (1-\beta) W_{kp} / \sum_{k=1}^{K} W_{kp}$$

Prioritizing metacells with respect to cellular states.

To prioritize metacells with respect to specified cellular states (committed or progenitor), a RWR algorithm was used based on the transition probability matrix G (ref. 67). RWR is a method that has been successfully used in numerous item prioritization tasks, such as web searches and characterizing disease-related genes (56, 68). The flexibility and robustness of RWR algorithms allowed us to prioritize cells/metacells with defined cellular states. The random walker starts from the vertex representing the metagene(s) and randomly moves to one of its neighbouring metacell or metagene, based on the transition probability described by G. Finally, the probability that the random walker reaching a metacell p converges to a scaled steady state $u_p$, where $\Sigma_p^P - 1 \mu_p = 1$, and all the metacell vertices in the graph are ranked by the steadystate probabilities. The R package igraph was used to perform the RWR with the default restarting probability 0.85 (ref. 69).

During the random walk, the parameter β regulates the probability of staying in the metagene graph. A large β encourages the random walker staying in the metacell graph $G_{MC}$, resulting in a sharper ranking results, whereas a small β encourages the random walker staying in the metacell-metagene graph $G_{MGMC}$ and $G_{MCMG}$, resulting in a more smoothened ranking. For the results reported in this study, β=0.85.

Gene Enrichment Score.

Genes were prioritized for a specified cellular state based on the correlation between their expression level in metacells and the steady-state probability u. Let $Y_{np}$ be the expression level of gene n in metacell p. The enrichment score of gene n in prioritized metacells for a specified cellular state was defined as:

$$ES_n = \sum_{p=1}^{P} \frac{Y_{np} + 1}{\sum_{i=1}^{N} (Y_{ip} + 1)} \left( u_p - \frac{1}{P} \sum_{j=1}^{P} u_j \right)$$

The enrichment score was the sum of steady-state probability (after scaled to mean of zero), weighted by the observed expression level. High enrichment score suggested high correlation between steady-state probability and expression levels.

Simulating single-cell RNA-seq expression data.

It was assumed the expected expression level of gene $n \in \{1, \ldots, N\}$ in cell $\in \{1, \ldots, M\}$, $$\mu_{nm} = \sum_{k=1}^{K} U_{nk} V_{km},$$

where V was randomly filled with 0 and 1 with probability 0.3 and 0.7, respectively, followed by the scaling each column so that $\Sigma_{k-1}^K V_{km}=1$ for each m, and $U_{nk}$ was randomly sampled from a Gamma distribution with fixed shape and rate. Let $D_{nm}$ be a binary indicator matrix of being a dropout event for gene n in cell m, where the dropout rate is 50%. The observed expression level of gene n in cell m is $X_{nm}$, followed a Poisson distribution with mean as $u_{nm}$ if $D_{nm}=0$, otherwise zero. In the experiments, the total number of genes and cells were set to 200 and 50, respectively.

Data Availability

The single cell RNA-seq data that support the findings of this study have been deposited in NCBI Sequence Read Archive (SRA) database with the project accession number PRJNA350294 (incorporated herein by reference). The dpath pipeline was implemented as an R package. Further, supplementary data and figures and aspects can be found in and through accessing Gong et al. Nat Commun. 2017 Feb. 9; 8:14362, which are also incorporated by reference herein in their entirety.

Results

Single-Cell RNA-Seq Analysis Using the Dpath Pipeline.

The dpath pipeline consists of four major steps. First, this program decomposes the expression profile matrix of single-cell RNA-seq into metagenes using wp-NMF. Second, dpath maps cells into metacells using a SOM algorithm. Third, the dpath algorithm prioritizes cells with respect to specific cellular states using a RWR algorithm on a heterogeneous metagene-metacell graph. Finally, this algorithm ranks genes for cellular states according to their expression profile.

NMF is distinguished from principal component analysis (PCA) by its use of non-negativity constraints (29). These constraints lead to a parts-based representation of subpopulations, instead of the holistic representations observed using PCA (29). To account for the dropout events, we used a weighted Poisson model as the cost function for NMF. The expected gene expression level was modelled as the linear combination of non-negative metagene basis and coefficients. The observed gene expression level was then modelled as a mixture of Poisson distribution of expected expression level and a dropout event represented by a low magnitude Poisson process (24). When decomposing the single-cell expression profile, wp-NMF gave each entry a different weight depending on the odds of being a dropout event. The simulation study suggested, that in the presence of the dropout noise, wp-NMP was superior to PCA in the separation of the cell clusters on the low dimensional space and with regards to the t-distributed stochastic neighbour embedding of top principal components (30).

wp-NMF was used to decompose the expression profile matrix of 281 Etv2-EYFPþ cells captured from E7.25, E7.75 and E8.25 into four metagenes (31). The expression matrix was therefore approximated by the product of non-negative metagene basis and coefficients. The metagene basis represented the contribution of each gene to each metagene, and the metagene coefficient, a probabilistic simplex that indicated the relative weight of each metagene in each cell, assigns distinct metagene signatures for individual cells (FIG. 1a).

To verify that this deconvolution strategy produced biologically relevant results, a list of selected genes with known expression patterns was first examined. The haematopoietic markers: Gata1, Ik2f1, Itga2b, Hba-a1, and Runx1, contributed to several metagenes, but primarily to the second metagene (MG2). The endocardial/cardiac genes: Gata4, Smarcd3, Tbx20, Alcam, and Dok4, contributed primarily to the third metagene (MG3) (32-34). The mesodermal marker, Pdgfra, also contributed significantly to MG3, consistent with the previous observations that Pdgfra is expressed in the cardiac mesoderm (35, 36). Also the previously described endocardial marker, Cgnl1, contributed to MG1 and MG3 metagenes. The endothelial markers, Plasmalemma vesicle associated protein (Plvap), Endomucin (Emcn) and Icam1 contributed primarily to MG1. Interestingly, other common endothelial markers, such as Pecam1, Cd34 and Cdh5, contributed broadly to a number of metagenes. The broad contribution of several haematopoietic and endothelial markers supported the notion that the current lineage markers for these populations are not specific. In contrast, the mesodermal lineage marker Brachyury (T) and Gli2, an effector of sonic hedgehog signaling pathway, contributed strongly to MG4. Moreover, Pou5f1 and Nanog that are expressed at the primitive steak stage (E7.25) contributed exclusively to MG4 (refs 37,38). The gene set enrichment analysis (GSEA) also suggested that genes that were specific to MG1 to MG4 were significantly associated with blood vessel development (GO:0001568), erythrocyte differentiation (GO:0030218), heart development (GO: 0007507) and stem cell maintenance (GO:0035019), respectively (FIG. 1b-e). Collectively, these data demonstrated that four metagenes represented the endothelial, haematopoietic, endocardial lineages and mesodermal progenitors, respectively.

Figure 2A:
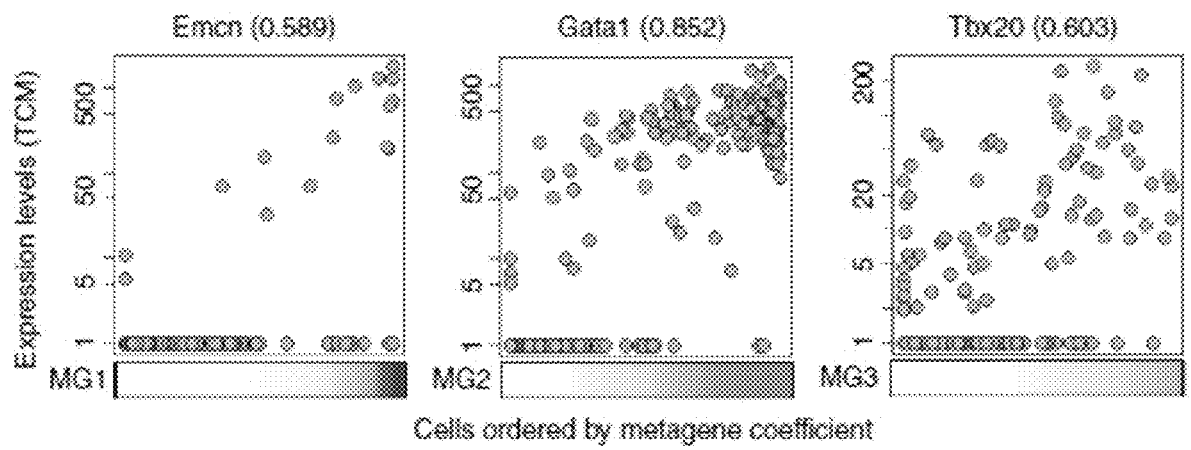
FIG. 2. The metagene signature using wp-NMF successfully separated cell clusters with distinct spatial distribution. (a) The scatter plot showed the relationship between the expression levels of Emcn, Gata1 and Tbx20 and the metagene coefficients of MG1 (endothelium), MG2 (blood) and MG3 (endocardium). The Pearson's correlation coefficients in the parenthesis were computed between the expression levels and the metagene coefficients. (b) Immunohistochemical techniques were used to locate cell populations identified by the metagene signature. A transverse section (at the level of the heart) of an E8.25 mouse embryo was stained using antibodies to EYFP, Endomucin (Emcn), Tbx20 and Gata1 (from left to right). Note that EYFP-positive populations segregated into three distinct populations, EYFP$^+$Emcn$^+$Tbx20$^-$Gata1$^-$ endothelial cells (closed arrowhead), EYFP$^+$Emcn$^+$Tbx20$^+$Gata1$^-$ endocardial cells (open arrowheads) and EYFP$^+$Emcn$^-$Tbx20$^-$Gata1$^+$ blood (small arrowheads). (c,d) Wp-NMF had superior performance for the separation of Emcn$^+$/Gata1$^-$/Tbx20$^-$, Emcn$^-$/Gata1$^+$/Tbx20$^-$ and Emcn$^-$/Gata1$^-$/Tbx20$^+$ among the Etv2-EYFP$^+$ cells compared with PCA, dimensionality reduction for zero-inflated single-cell gene expression analysis, diffusion map and t-distributed stochastic neighbour embedding. In both panels, x axis indicated the number of hidden dimensions (K), and the y axis represented (c) leave-one-out cross validation (LOO-CV) error and (d) WSS (within-cluster sum of squares)/TSS (total sum of squares) ratio.
Figure 2B:
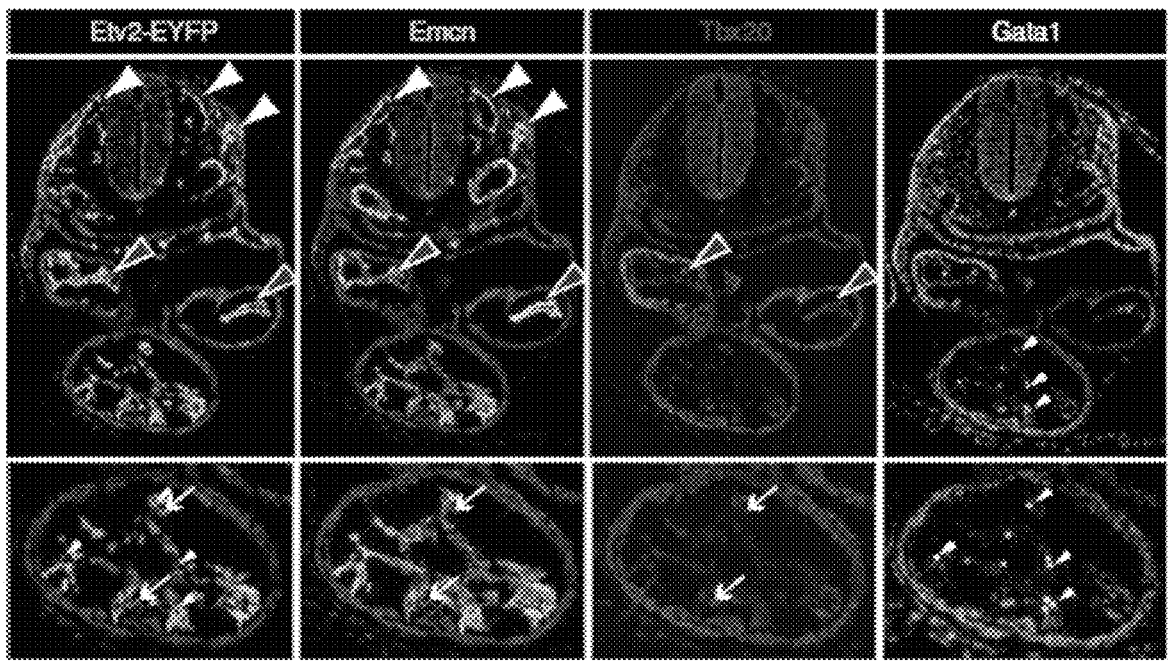
Figure 2C:
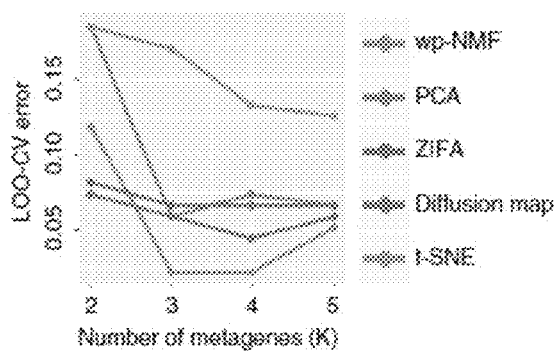
Figure 2D:
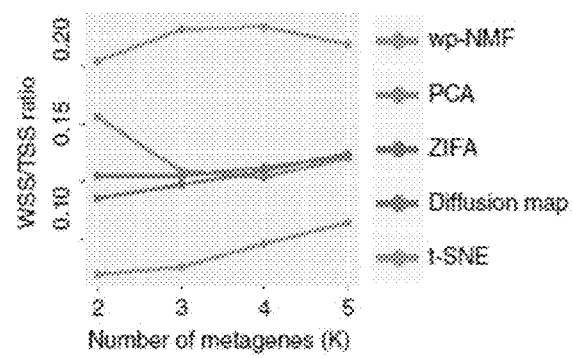

The observation that the single cells carrying different metagene signatures associated with different biological functions prompted the hypothesis that the cells with a distinct metagene signature had a distinct spatial distribution. To experimentally test this hypothesis, Emcn, Gata1 and Tbx20 were identified as the distinguishing marker genes for MG1 (endothelium), MG2 (blood) and MG3 (endocardium). Expression levels of these genes were strongly positively correlated with the metagene intensity of MG1, MG2 and MG3, respectively (FIG. 2a). Immunohistochemical staining demonstrated that the Etv2-EYFP$^+$ cells segregate into three distinct subpopulations defined by these markers, namely, those exclusively marked by (1) Emcn (Etv2$^+$/Emcn$^+$/Gata1$^-$/Tbx20$^-$), (2) Gata1 (Etv2$^+$/Emcn$^-$/Gata1þ/Tbx20$^-$) and (3) Tbx20 (Etv2$^+$/Emcn$^-$/Gata1$^-$/Tbx20$^+$). These subgroups showed distinct spatial distribution in the E7.75 embryo (FIG. 2b) and confirmed that MG1 represented the endothelium, MG2 represented the blood and MG3 the endocardium. These results indicated that the metagene signature determined by wp-NMF was able to successfully separate three cell clusters with distinct spatial distribution. Moreover, wp-NMF had superior performance for the separation of these three spatially distinct Etv2-EYFP þ cell populations compared with other popular factorization and dimension reduction tools, such as PCA, dimensionality reduction for zero-inflated single-cell gene expression analysis, diffusion map and t-distributed stochastic neighbour embedding. To make these comparisons, the leave-one-out cross-validation (LOO-CV) was used and within-cluster sum of squares (WSS) to total sum of squares (TSS) ratio (FIG. 2c,d) (30, 39, 40).

Identification of Progenitor and Committed Cells Using Dpath.

The metagene coefficient indicates the expression profile of each metagene in each cell. For example, MG1, MG2 and MG3 dominated isolated groups of cells (FIG. 1a). Alternatively, multiple metagenes could also be expressed in a single cell, suggesting that this cell harbored the gene signature of multiple lineages and is multipotent with regards to lineage commitment.

Figure 3A:
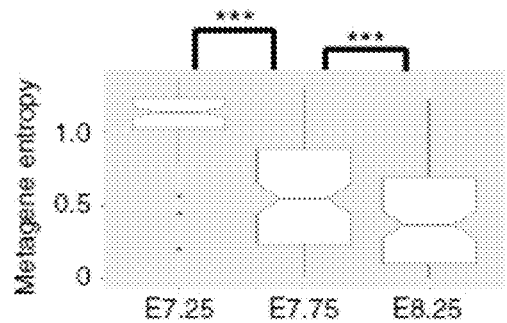
FIG. 3. The metacell landscape and cluster analysis identified Etv2 derivatives. (a) The cells from E7.25 had significantly higher metagene entropy than the cells from E7.75, and the metagene entropy of E7.75 cells was significantly higher than E8.25 cells (Wilcoxon rank-sum test, P value=1.2E-10 and P value=0.00075). (b) The distribution of metagene entropy of metacells is shown on the SOM. White colour represents high entropy metacells and red colour represents low entropy metacells. (c) A schematic represents a simplified version of the expected differentiation pathway with the dominant metagenes represented by colour for populations we expected to observe. (d) PAM algorithm clusters metacells by partitioning the metacell. The colour indicates the expression intensity of each metagene in the metacells. (e) Eight major cell clusters were identified by partitioning the metacell landscape. Each cell was mapped to the metacell with the most similar metagene coefficients. (1) The table indicates the time sources of cells from each cluster. (2) The heatmap shows the average metagene coefficients of each cell cluster.

Indeed, marker genes that are abundantly expressed in the committed lineages tend to be expressed in their common progenitor cells but at a lower level (19, 41). Thus the concept of metagene entropy was introduced as a novel tool to use the heterogeneity of gene expression signature of a single cell to predict the differentiation state of the cell (42). Entropy is used in statistical mechanics and information theory as a measure of disorder or uncertainty. It was hypothesized that cells with high metagene entropy have higher differentiation potential than cells with low metagene entropy. The analysis using two published single-cell RNA-seq data sets on lung epithelium development and mouse fibroblasts reprogramming suggested metagene entropy was indeed significantly higher in progenitor cells compared with more differentiated cells (19, 43). Following the application of metagene entropy to the Etv2$^+$ cells, it was noted that the cells from E7.25 had significantly higher metagene entropy than the cells from E7.75, and the metagene entropy of E7.75 cells was significantly higher than E8.25 cells (Wilcoxon rank-sum test, P-value=1.2E-10 and P-value=0.00075). This finding was consistent with the general consensus that cells from early developmental stages have higher differentiation potency than from the later stages (FIG. 3a). This is the first method in this field of single-cell RNA-seq analysis that establishes a quantitative measurement of cellular (progenitor versus committed) state.

Figure 3B:
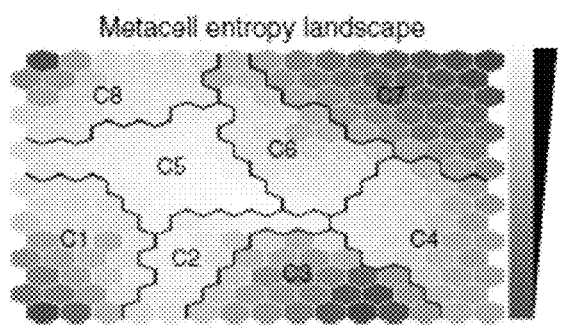
Figure 3C:
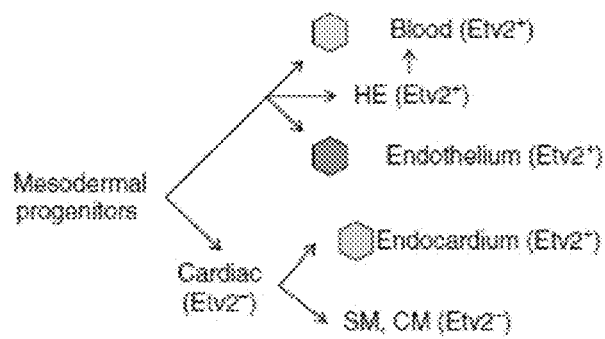

Establishing the metacell landscape for Etv2 derivatives. Although metagene entropy was defined and established the directionality of the developmental programme, another requirement was introduced such that the metagene expression profiles between cells in the neighbouring developmental stages are similar. A SOM algorithm was used to organize Etv2$^+$ cells with similar metagene coefficients into a hexagonal grid and visualized the lineage structures in a 15× 15 two-dimensional (2D) map. The SOM is an unsupervised machine learning method that was developed to cluster and visualize the high dimensional data and has been widely used in bioinformatics because of its superb visualization capability (44). In this application, each hexagonal grid on the SOM was defined as a metacell, and each cell was mapped to the metacell with the most similar metagene expression pattern. The analysis revealed a graded distribution of metagene entropy on the SOM: in the central region of the SOM, the metacells had higher metagene entropy than those at the periphery or corners, and the region with the highest metagene entropy was enriched by the cells from E7.25. In contrast, the region with low metagene entropy was associated with more cells from the later developmental stages, E7.75 and E8.25 (FIG. 3b). Moreover, the committed haematopoietic, endothelial and endocardial lineages were clearly separated or located at the edges and corners of the SOM (FIG. 3c,d). This metacell landscape therefore represented the lineage relationships reminiscent of the branching valleys of the epigenetic landscape envisioned by Waddington (45).

Figure 3D:
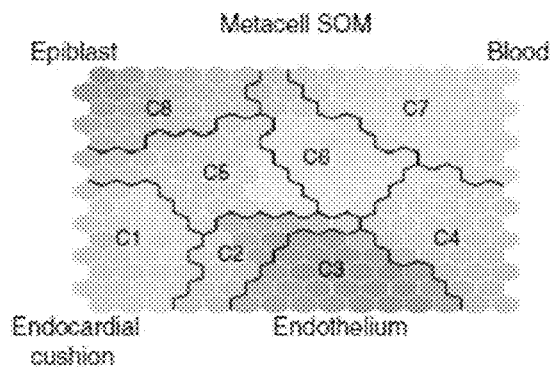
Figure 3E:
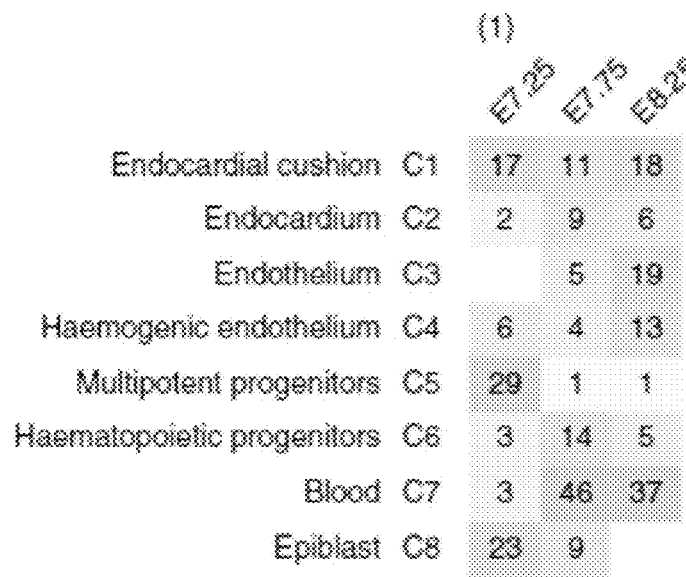

Next, to reveal the identity of the major populations of Etv2-EYFP$^+$ cells, all 281 cells were clustered into 8 cell clusters by partitioning the SOM using the Partitioning Around Medoids (PAM) algorithm (FIG. 3d,e). Among these cell clusters, C2, C4, C5 and C6 that expressed multiple metagenes were enriched in earlier time points (E7.25 and E7.75) and therefore, it was hypothesized, represent the more progenitor-like cellular states. In contrast, C1, C3 and C7 expressed primarily the endocardial (MG3), endothelial (MG1) and haematopoietic (MG2) metagenes, respectively, and as such had relatively low average metagene entropy, supporting the notion that these cell clusters represent more differentiated cells (FIG. 3b). C8 is a unique population that is found abundantly in E7.25 and disappears at later stages. As this population expresses pluripotency markers and very low level of Etv2 and EYFP (enhanced yellow fluorescent protein) compared with other populations, it was hypothesize that these cells represent descendants of early blastomeres and epiblasts that express Etv2 at low levels or stochastically (46).

It was found that the metacells with the highest entropy in the cell population were positive for T (C5, highest expressors are marked with asterisks). This T$^+$ group of cells clustered adjacent to the common haematopoietic and endothelial progenitors (highlighted in yellow) and represented the most immature progenitors present in our Etv2-EYFP population. The metacells with highest entropy in C5 (demarcated by yellow lines) expressed Etv2, Kdr, Sox7, Runx1, Gata1 and Snca. Interestingly, these progenitors represented cells that expressed Sox7 and Runx1. The central location of these cells suggested that they were the earlier progenitors. In contrast, more mature cells of the haematopoietic and endothelial lineages segregated to peripheral locations. These peripherally located cells expressed Hbb-y, Car1 and Hba-a1, which are the mature markers of the haematopoietic lineage (C7), and Emcn, Plvap, and Nos3, which are the mature markers of the endothelial lineage (C3), respectively.

Towards the lower left corner of the SOM, metacells enriched in endocardial/cardiac mesodermal genes (Tbx20 and Pdgfra) were localized. As these cells were isolated based on EYFP expression driven by the Etv2 promoter, it is likely that C2 represents endocardium. To examine this hypothesis, the expression of Cgnl1 and Dok4 was analyzed, which are reported to be enriched in endocardium (47). It was observed that both Cgnl1 and Dok4 were expressed in C2 population. The segregation of the putative endocardium from the haematopoietic and endothelial lineages is consistent with previous reports that endocardium is derived from cardiac mesoderm (FIG. 3c) (48).

Biological Verification of the Dpath Pipeline Output.

The data demonstrated that, by combining the biologically relevant metagene signature, metagene entropy and the metacell landscape, the dpath pipeline provided a straightforward way to examine the lineage relationships of underlying single cells. Here, two predictions from analyzing the metacell landscape of Etv2-EYFP$^+$ single cells were experimentally verified.

Identification of Endocardial Cushion Progenitors.

Figure 4A:
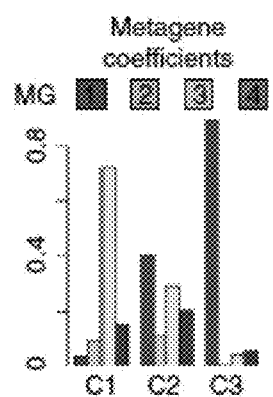
FIG. 4. Immunohistochemical and ES/EB studies support the dpath results. (a) The average metagene coefficients of cells from the C1, C2 and C3 clusters were illustrated using the barplot. In contrast to C2 where both MG1 (endothelium) and MG3 (endocardium) had high intensity, C1 and C3 were dominated by MG3 and MG1, respectively. (b) Immunohistochemical analysis of Etv2-EYFP transgenic hearts at E7.75 and E8.5 supports the existence of the C2 cell population and the notion that they are progenitors of the cardiac cushion. Fluorescent images are pseudo-coloured after photographing in black and white. Large arrowheads point to EYFPþ Endomucinþ endothelial cells. Small arrowheads denote EYFPþ Endomucinþ angioblasts. Small arrows highlight EYFP$^+$Tbx20$^+$ Endomucin$^-$ C1 cells (a: common atrium, cc: cardiac crescent, ec: endocardium, ivs: intraventricular septum, la: left atrium, lv: left ventricle, nt: neural tube, oft: outflow tract, ra: right atrium, rv: left ventricle). Scale bars indicate 100 mm. (c,d) The expression patterns of Runx1 and Gata1 were illustrated on the metacell landscape. Green: high expression. Black: low expression. (e,f) The aggregated expression pattern of genes related to primitive erythrocyte differentiation (GO:0060215) and definitive erythrocyte differentiation (GO:0060216) were illustrated on the metacell landscape. Yellow: high expression. Blue: low expression. (g) The barplot shows the top 10 KEGG pathways that were enriched in genes that were significantly upregulated in C2, C5 and C6 cell clusters, compared with the remaining clusters (SCDE P value<0.001). (h) The aggregated expression pattern of genes related to hedgehog signalling pathway were illustrated on the metacell landscape. (i) A schematic diagram represents the ES/EB differentiation model system (using Etv2-EYFP transgenic cell lines) and the exposure to the SHH agonist (SAG) or SHH antagonist cyclopamine from days 2 to 4.5. (j) FACS quantification indicates that sonic hedgehog agonist (SAG) (or cyclopamine) significantly promotes (or suppresses) endothelial and haematopoietic progenitors (EYFP$^+$/CD41$^+$/Tie2$^+$), compared with dimethyl sulfoxide control (*Student's t-test P value<0.05).
Figure 4B:
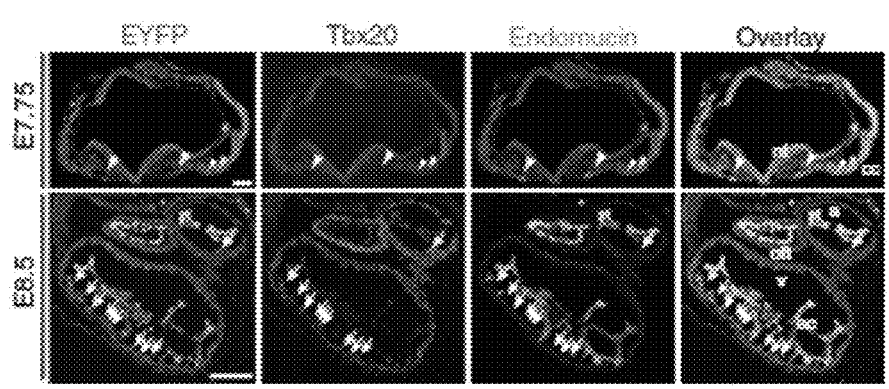

C1, C2 and C3 clusters were first compared, which were particularly intriguing. C2 had the metagene signature for endothelial, cardiac and mesodermal progenitors (MG1, MG3 and MG4), while C1 and C3 were dominated by the endocardial (MG3) and endothelial (MG1) metagenes, respectively (FIG. 4a). On the SOM, C2 connected C1 and C3 clusters and it had higher metagene entropy (FIG. 3b). It was then predicted that the C2 population was the progenitors of the C1 population, according to their metagene coefficients and metagene entropy change. The gene profile analysis revealed that the general gene expression change was C2 (Etv2-EYFP$^+$, Cardiac$^+$, Endothelial$^+$)-C1 (Etv2-EYFP$^+$, Cardiac$^+$, Endothelial). This transition is similar to the endothelial-mesenchymal transition involved in the generation of cardiac cushion from the endocardium (49). By using Emcn and Tbx20 as markers for MG1 and MG3, respectively, the immunohistochemical experiments confirmed the existence of the C2 cell populations and supported that the C2 population were progenitors of the cardiac cushion that originated from endocardium, and the molecular transition (that is, changes in gene expression profile) occurred as early as E8.25 (FIG. 4b).

Identification of Two Waves of Haematopoiesis.

Figures 4C, 4D:
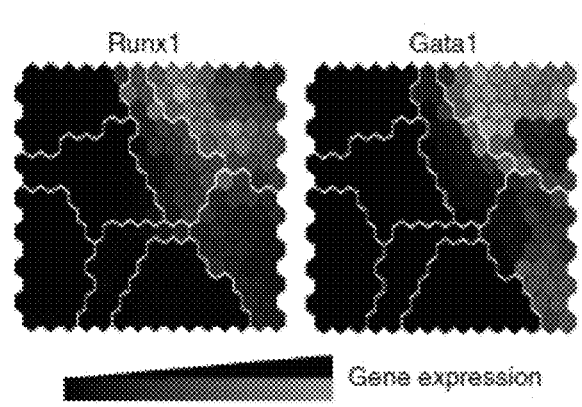
Figures 4E, 4F:
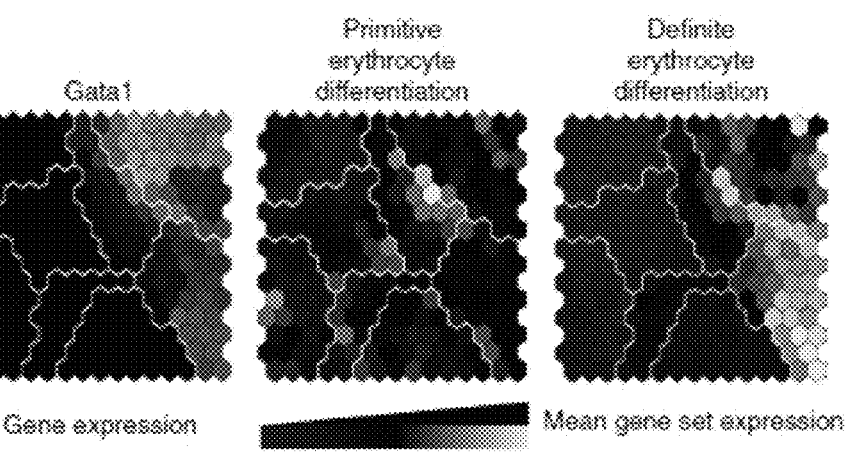

Next, the paths leading to haematopoiesis were examined. It was observed that, on the SOM, between the highest entropy cell cluster C5 and the committed haematopoietic cluster C7, there existed a transitional cell cluster C6 with metagene entropy between C5 and C7, predicting that the differentiation path is C5-C6-C7. Within the C6 cluster, Runx1 was expressed in most of the C6 metacells, while Gata1 was only expressed in a few metacells near the border with C7 (FIG. 4c,d). This order of gene expression is consistent with the observation that Runx1 expression precedes Gata1 expression during primitive haematopoiesis (50). C4 is another group that neighbours C7. The C4 cell cluster also had relatively higher metagene entropy than C7 and harbored the endothelial and haematopoietic metagenes; C4 had relatively stronger expression of genes related to definite erythrocyte differentiation (GO:0060216) than those related to primitive erythrocyte differentiation (GO:0060215), thus the C4 cell cluster represents the haemogenic endothelial lineage (FIG. 4e,f).

Endothelial Differentiation.

The C2 cell cluster was located between C5 and the committed endothelial cluster C3 and had an intermediate metagene entropy levels and served as a transition state between C5 and C3. Therefore, C5-C2-C6 transition represents the early differentiation of endothelial lineages.

Identification of Pathways for Haematoendothelial Bifurcation.

Figure 4G:
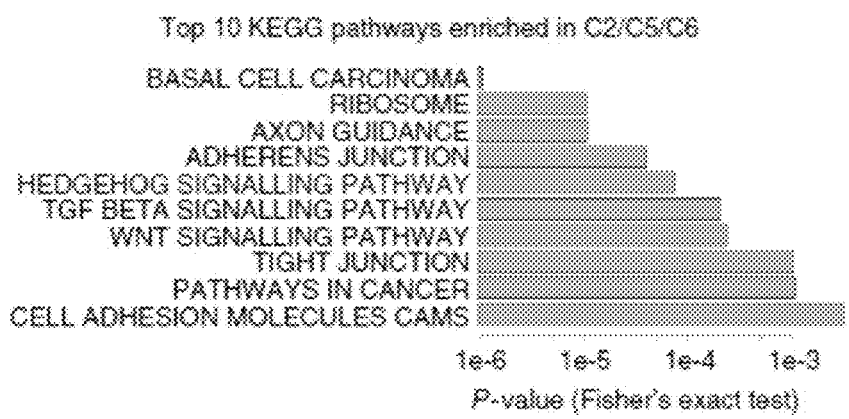
Figure 4H:
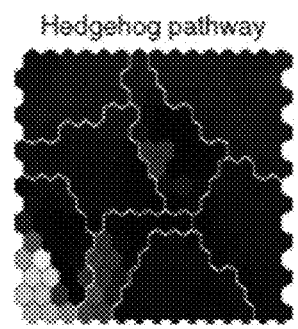
Figure 4I:
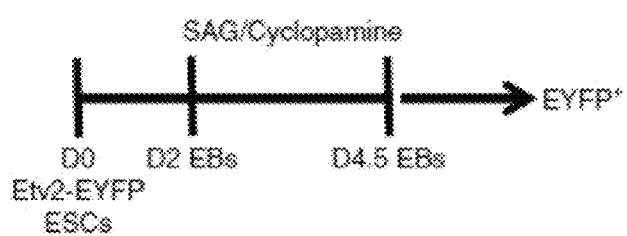
Figure 4J:
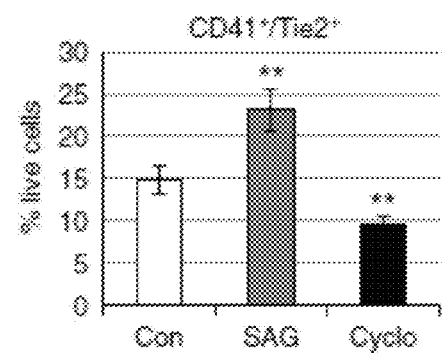

It was hypothesized that the signalling pathways enriched in clusters C2, C5 and C6 have functional roles in the haemato-endothelial development. 132 genes were identified that were significantly upregulated in progenitor cellular clusters C2, C5 and C6, compared with the other five clusters (SCDE P value<0.001) (24), and 21 KEGG pathways that were enriched in these upregulated genes (Fisher's exact test P value<0.05). Sonic signaling pathway (SHH) ranked as the fifth most enriched pathways in C2/C5/C6 (FIG. 4g,h). SHH has functions during development and regeneration (51). To examine the roles of the SHH pathway in haemato-endothelial differentiation, an ES/embryonic body (EB) differentiation model system was used and exposed them to SHH agonist (SAG) or the SHH antagonist cyclopamine from days 2 to 4.5 (FIG. 4i). At day 4.5, FACS analysis was undertaken for the Etv2-EYFP$^+$ cells from respective ES/EBs and analyzed them for endothelial and haematopoietic markers. Compared with the dimethyl sulfoxide control, it was observed that the SHH agonist significantly promoted the endothelial and haematopoietic progenitor cells (CD41$^+$/Tie2$^+$), while cyclopamine significantly suppressed this cell population (FIG. 4j). The SHH agonist and antagonist also had similar effects on differentiated endothelial (Tie2$^+$/CD31$^+$) and haematopoietic (CD41$^+$/CD45$^+$) lineages. These experiments confirmed SHH as a key signaling pathway that regulates the differentiation of haemato-endothelial lineages (52-55). The studies further established a new role for hedgehog signalling in the regulation of the haemato-endothelial (Etv2$^+$Tie2$^+$ CD41$^+$) progenitors (FIG. 4i,j).

Discovery of Trajectory from Progenitor to Committed State.

After organizing cells into a SOM such that neighbouring metacells had a similar metagene expression pattern and establishing metagene entropy as a means to add directionality to the differentiation process, next quantitatively assessed the progenitor and committed states on the metacell SOM and predicted the developmental trajectories. A heterogeneous metacell-metagene probability graph (a transition matrix) was built to describe the probability of transitioning from a metagene to a metacell (or vice versa) or from a metacell to another metacell. A metacell was considered as a parent (progenitor) of its neighbouring metacell on the SOM only if its metagene entropy was higher than that of the derivative metacell. Second, a RWR algorithm was used on the heterogeneous graph to infer the probability of a metacell being in a committed state to one metagene or being in a progenitor state with the ability to transition to multiple metagenes (56). Once the most likely progenitor and committed states (metacells) were identified, developmental trajectories from the progenitor cellular states toward the committed cellular states of endothelium, blood and endocardium were determined as the shortest paths between them on the SOM (FIG. 5a).

First, the inferred the progenitor and committed cellular states were first verified. The genes were ranked according to the similarity between their metacell expression profiles and the probability of being a specific cellular (progenitor or committed) state of the metagene(s). The GSEA suggested that regulation of vasculature development (GO:1904018), erythrocyte differentiation (GO:0030218) and epithelial to mesenchymal transition (GO:0001837) related genes were significantly enriched at the top ranking genes for the committed metacells for the first, second and third metagenes, while the cell fate commitment (GO:0045165) related genes were significantly correlated with both MG3 and MG4, which was consistent with the previous determination of metagene fates based on known marker genes (57). The GSEA of known mouse phenotypic-related genes suggested similar functional separations of metagenes. To further confirm the biological relevance of genes that are enriched in predicted progenitor cellular states, a previously published Etv2 chromatin immunoprecipitation sequence data set was examined and it was found that the genes that had experimentally verified 3,953 highly confident (common in their V5 and PolyAb experiments) Etv2-binding sites (at least one chromatin immunoprecipitation sequence hit within −5,000 to +1,000 bp region surrounding the transcription start sites of at least one transcript) had significantly greater prioritization scores than those that did not (Wilcoxon rank-sum test, P value<$1.0 \times 10^{-20}$) (58). These results verified the biological relevance of progenitor and committed cellular states inferred by the RWR algorithm.

Second, by examining the expression of three known lineage marker genes (Emcn, Gata1 and Tbx20) along the dpath's developmental trajectories, it was found that Emcn, Gata1 and Tbx20 were upregulated along the endothelial path (P1), haematopoietic path (P2) and endocardial path (P3) (FIG. 5b). A head-to-head comparison was then conducted and evaluated whether currently available methods can predict the trajectories that were obtained. Results show that Monocle, Wishbone and Mpath were not able to infer the pseudotemporal or developmental trajectories that agree with the current biological knowledge. Moreover, to quantitatively evaluate the accuracy of inferred pseudotime, it was counted how often a pseudotime puts a cell from a later temporal sorting before an earlier one (measured by Kendall rank correlation coefficient). It was found that there existed a strong positive correlation between temporal labels (E7.25, E7.75 and E8.25) and dpath's pseudotime (mean Kendall rank correlation coefficient¼ 0.798), which was noticeably higher than popular pseudotime inference algorithms such as Monocle (0.213) and Wishbone (0.375) (FIG. 5c, Mpath was excluded from this comparison as the pseudotime could not be automatically calculated).

Taken together, the GSEA of genes that were enriched in committed and progenitor cellular states confirmed the biological significance of developmental trajectories predicted by dpath, and the results also suggested that the predicted pseudotime was more accurate than Monocle and Wishbone.

DISCUSSION

Herein is described the use of the dpath pipeline to decompose single-cell RNA-seq data with the awareness of dropout events. Three major technical breakthroughs are provided to the single-cell analysis technology that includes: (1) a method to fill in dropout events; (2) a method to rank the differentiation potential using the metagene entropy, and (3) a method to visualize the differentiation paths on a 2D map. This method was used to prioritize committed and progenitor states for haematopoietic, endocardial and endothelial lineages obtained from 281 $Etv2^+$ cells and ranked genes for distinct cellular states, especially for progenitor endothelial and haematopoietic states.

The first unique feature of dpath is applying wp-NMF for decomposing single-cell RNA-seq data. The use of the weighted Poisson model as the cost function reduced the impact of dropout events on matrix decomposition by maximizing the usage of informative genes that have a high probability of being expressed. The other advantage of NMF-based matrix decomposition method, compared with PCA, is that NMF yields a sparse parts-based representation of gene expression profiles (31). Just as NMF is able to distinguish different meanings of words used in different contexts, metagene basis and coefficients can overlap and thus expose the participation of a single gene in multiple pathways and account for the activity of multiple pathways in a single cell. As a result of the parts-based representation, the metagene entropy, the entropy of metagene coefficients after proper scaling, serves as a measure of how many distinct programmes (parts) are active (expressed) in a cell. A cell with high metagene entropy implies that multiple programmes (represented by metagene basis) participate in the cellular activity, leading to a high uncertainty with respect to the lineage commitment and thus high level of cellular plasticity (59). dpath was applied to publicly available single-cell data sets and a head-to-head comparison was undertaken with conventional programs. It was demonstrated the superiority of dpath as it accurately predicted differentiation states and had higher resolution than previously published methods. Although entropy has been described as a potential measure for the uncertainty concerning the cellular state, this is the first study to establish an entropy-based method to measure the multipotency in the context of single-cell expression analysis (42).

Another unique feature of our new package dpath is that it represents the cellular states on a 2D SOM where metacells with similar metagene expression profiles are grouped together. This not only provides an intuitive way to visualize the distribution of cellular states from the input cells but also reduces the impact of dominant lineages in the analysis. Another feature of this method is that one metacell is allowed to have multiple parental states, and globally, there can be multiple progenitor states that can give rise to individual committed states. This provides additional flexibility of modelling lineage hierarchies than organizing cells into a lineage tree-like structure where all individual committed states originate from one single cell, because single-cell transcriptome analysis represents a snapshot of cells present at experimental time points (E7.25, E7.75 or E8.25, in this case), and any given cell is unlikely to be a descendant of similar cells present at the same time. Therefore, SOM reflects continuous differentiation paths of multiple cells that are asynchronously differentiating towards the same differentiated state.

To further examine the dpath algorithm, a subpopulation of the Etv2-expressing cells were interrogated during murine embryogenesis. The high entropy progenitor cells of the haematopoietic and the endothelial lineages that we have identified are of intense interest, with respect to lineage specification. At E7.25 (early streak), E7.75 (late streak-late allantoic bud stage (60)) and E8.25 (linear heart loop stage), $Etv2\text{-}EYFP^+$ cells are present in endothelial cells and primitive erythrocytes of the yolk sac blood islands (extraembryonic) and embryonic blood vessels, including dorsal aortae, endocardium and migrating angioblasts (14). Moreover, previous studies are consistent with the notion that prior to gastrulation epiblast cells are largely unspecified, and the signals they encounter as they ingress through the primitive streak specifies their fate (60, 61). New mesodermal cells emerging from the streak are still plastic but commit quickly to specific lineages based on the signals they received in the primitive streak. Differential enrichment of multiple signalling pathways in haematopoietic and endothelial metacells indicate that these are candidates that cells encounter as they pass through the primitive streak. In the present study, dpath was used to successfully identify the dynamic expression pattern of the members of SHH signalling pathway and experimentally verify its critical roles in haemato-endothelial lineage differentiation. It is recognized that the number of profiled cells was relatively small compared with the total population of $Etv2^+$ cells in vivo, especially for the later time point E8.25. Although the major developmental trajectories were successfully identified within the $Etv2^+$ cells, addition of more single cells will reveal further subpopulations within committed endothelial, endocardial and haematopoietic lineages.

In summary, using the dpath pipeline, single-cell RNA seq data was clustered without using previously known information, which was then verified by gene expression analysis and functional analysis. The expression patterns of known genes and calculated metagene entropy were consistent with known differentiation pathways of haematopoietic and endothelial cells. The data are significant in multiple ways. First, the full transcriptome of individual $Etv2^+$ cells was provided, which was not available previously. This is important as many genes are commonly expressed in haematopoietic and endothelial lineages. Cell surface markers commonly used to distinguish them from each other or their progenitors are not highly specific. The transcriptome of single cells was analyzed and that provides information for identifying novel markers of these cell populations to improve the purity of populations for transcriptome and functional analyses. Second, differentiation paths from progenitors to more mature cells were identified using the novel concept of metagene entropy. The gene expression observations within the SOM differentiation paths validate the method and attests that this concept is an excellent approximation of the differentiation process. We predict that this method will be able to reconstruct differentiation pathways with any data set, including different populations and broader, heterogeneous data sets. Third, pathway enrichment analysis based on the results identified signaling pathways and molecules that were not previously identified as well as those that have been previously identified. The dpath pipeline is provided in a downloadable R package. This is a tool to extract meaningful information from exponential amounts of RNA-seq data produced daily.

BIBLIOGRAPHY

1. Schmeisser, A. & Strasser, R. H. Phenotypic overlap between hematopoietic cells with suggested angioblastic potential and vascular endothelial cells. J. Hematother. Stem Cell Res. 11, 69-79 (2002).
2. Shalaby, F. et al. A requirement for Flk1 in primitive and definitive hematopoiesis and vasculogenesis. Cell 89, 981-990 (1997).
3. Shalaby, F. et al. Failure of blood-island formation and vasculogenesis in Flk-1-deficient mice. Nature 376, 62-66 (1995).
4. Robb, L. et al. Absence of yolk sac hematopoiesis from mice with a targeted disruption of the scl gene. Proc. Natl Acad. Sci. USA 92, 7075-7079 (1995).
5. Shivdasani, R. A., Mayer, E. L. & Orkin, S. H. Absence of blood formation in mice lacking the T-cell leukaemia oncoprotein tal-1/SCL. Nature 373, 432-434 (1995).
6. Visvader, J. E., Fujiwara, Y. & Orkin, S. H. Unsuspected role for the T-cell leukemia protein SCL/tal-1 in vascular development. Genes Dev. 12, 473-479 (1998).
7. Stainier, D. Y., Weinstein, B. M., Detrich, H. W., Zon, L. I. & Fishman, M. C. Cloche, an early acting zebrafish gene, is required by both the endothelial and hematopoietic lineages. Development 121, 3141-3150 (1995).
8. Dumont, D. J. et al. Dominant-negative and targeted null mutations in the endothelial receptor tyrosine kinase, tek, reveal a critical role in vasculogenesis of the embryo. Genes Dev. 8, 1897-1909 (1994).
9. Sato, T. N. et al. Distinct roles of the receptor tyrosine kinases Tie-1 and Tie-2 in blood vessel formation. Nature 376, 70-74 (1995).
10. Takakura, N. et al. Critical role of the TIE2 endothelial cell receptor in the development of definitive hematopoiesis. Immunity 9, 677-686 (1998).
11. De Val, S. et al. Combinatorial regulation of endothelial gene expression by ets and forkhead transcription factors. Cell 135, 1053-1064 (2008).
12. Ferdous, A. et al. Nkx2-5 transactivates the Ets-related protein 71 gene and specifies an endothelial/endocardial fate in the developing embryo. Proc. Natl Acad. Sci. USA 106, 814-819 (2009).
13. Lee, D. et al. ER71 acts downstream of BMP, Notch, and Wnt signaling in blood and vessel progenitor specification. Cell Stem Cell 2, 497-507 (2008).
14. Rasmussen, T. L. et al. ER71 directs mesodermal fate decisions during embryogenesis. Development 138, 4801-4812 (2011).
15. Palencia-Desai, S. et al. Vascular endothelial and endocardial progenitors differentiate as cardiomyocytes in the absence of Etsrp/Etv2 function. Development 138, 4721-4732 (2011).
16. Koyano-Nakagawa, N. et al. Etv2 is expressed in the yolk sac hematopoietic and endothelial progenitors and regulates lmo2 gene expression. Stem Cells 30, 1611-1623 (2012).
17. Scialdone, A. et al. Resolving early mesoderm diversification through single-cell expression profiling. Nature 35, 289-293 (2016).
18. Li, G. et al. Transcriptomic profiling maps anatomically patterned subpopulations among single embryonic cardiac cells. Dev. Cell 39, 491-507 (2016).
19. Treutlein, B. et al. Reconstructing lineage hierarchies of the distal lung epithelium using single-cell RNA-seq. Nature 509, 371-375 (2014).
20. Usoskin, D. et al. Unbiased classification of sensory neuron types by large-scale single-cell RNA sequencing. Nat. Neurosci. 18, 145-153 (2014).
21. Ohnishi, Y. et al. Cell-to-cell expression variability followed by signal reinforcement progressively segregates early mouse lineages. Nat. Cell Biol. 16, 27-37 (2014).
22. Tang, F. et al. Tracing the derivation of embryonic stem cells from the inner cell mass by single-cell RNA-Seq analysis. Cell Stem Cell 6, 468-478 (2010).
23. Trapnell, C. et al. The dynamics and regulators of cell fate decisions are revealed by pseudotemporal ordering of single cells. Nat. Biotechnol. 32, 381-386 (2014).
24. Kharchenko, P. V., Silberstein, L. & Scadden, D. T. Bayesian approach to single-cell differential expression analysis. Nat. Methods 11, 740-742 (2014).
25. Gruˆn, D., Kester, L. & van Oudenaarden, A. Validation of noise models for single-cell transcriptomics. Nat. Methods 11, 637-640 (2014).
26. Gru¨n, D. et al. De novo prediction of stem cell identity using single-cell transcriptome data. Cell Stem Cell 19, 266-277 (2016).
27. Setty, M. et al. Wishbone identifies bifurcating developmental trajectories from single-cell data. Nat. Biotechnol. 34, 637-645 (2016).
28. Chen, J., Schlitzer, A., Chakarov, S., Ginhoux, F. & Poidinger, M. Mpath maps multi-branching single-cell trajectories revealing progenitor cell progression during development. Nat. Commun. 7, 11988 (2016).
29. Lee, D. D. & Seung, H. S. Learning the parts of objects by non-negative matrix factorization. Nature 401, 788-791 (1999).
30. Van der Maaten, L. & Hinton, G. Visualizing data using t-SNE. J. Mach. Learn. Res. 9, 85 (2008).
31. Brunet, J. P., Tamayo, P., Golub, T. R. & Mesirov, J. P. Metagenes and molecular pattern discovery using matrix factorization. Proc. Natl Acad. Sci. USA 101, 4164-4169 (2004).
32. Heikinheimo, M., Scandrett, J. M. & Wilson, D. B. Localization of transcription factor GATA-4 to regions of the mouse embryo involved in cardiac development. Dev. Biol. 164, 361-373 (1994).
33. Lou, X., Deshwar, A. R., Crump, J. G. & Scott, I. C. Smarcd3b and Gata5 promote a cardiac progenitor fate in the zebrafish embryo. Development 138, 3113-3123 (2011).
34. Barnes, R. M., Firulli, B. A., Conway, S. J., Vincentz, J. W. & Firulli, A. B. Analysis of the Hand1 cell lineage reveals novel contributions to cardiovascular, neural crest, extraembryonic, and lateral mesoderm derivatives. Dev. Dyn. 239, 3086-3097 (2010).
35. Kataoka, H. et al. Expressions of PDGF receptor alpha, c-Kit and Flk1 genes clustering in mouse chromosome 5 define distinct subsets of nascent mesodermal cells. Dev. Growth Differ. 39, 729-740 (1997).
36. Bondue, A. et al. Defining the earliest step of cardiovascular progenitor specification during embryonic stem cell differentiation. J. Cell Biol. 192, 751-765 (2011).
37. DeVeale, B. et al. Oct4 is required BE7.5 for proliferation in the primitive streak. PLoS Genet. 9, e1003957 (2013).

38. Hart, A. H., Hartley, L., Ibrahim, M. & Robb, L. Identification, cloning and expression analysis of the pluripotency promoting Nanog genes in mouse and human. Dev. Dyn. 230, 187-198 (2004).
39. Pierson, E. & Yau, C. ZIFA: dimensionality reduction for zero-inflated single cell gene expression analysis. Genome Biol. 16, 241 (2015).
40. Haghverdi, L., Buettner, F. & Theis, F. J. Diffusion maps for high-dimensional single-cell analysis of differentiation data. Bioinformatics 31, 2989-2998 (2015).
41. Heinâniemi, M. et al. Gene-pair expression signatures reveal lineage control. Nat. Methods 10, 577-583 (2013).
42. MacArthur, B. D. & Lemischka, I. R. Statistical mechanics of pluripotency. Cell 154, 484-489 (2013).
43. Kim, D. H. et al. Single-cell transcriptome analysis reveals dynamic changes in lncRNA expression during reprogramming. Cell Stem Cell 16, 88-101 (2015).
44. Kohonen, T. Self-Organizing Maps (Springer, 2001).
45. Waddington, C. H. The Strategy of the Genes 20 (2015).
46. Kageyama, S. I., Liu, H., Nagata, M. & Aoki, F. The role of ETS transcription factors in transcription and development of mouse preimplantation embryos. Biochem. Biophys. Res. Commun. 344, 675-679 (2006).
47. Narumiya, H. et al. Endocardiogenesis in embryoid bodies: novel markers identified by gene expression profiling. Biochem. Biophys. Res. Commun. 357, 896-902 (2007).
48. Misfeldt, A. M. et al. Endocardial cells are a distinct endothelial lineage derived from Flk1þ multipotent cardiovascular progenitors. Dev. Biol. 333, 78-89 (2009).
49. von Gise, A. & Pu, W. T. Endocardial and epicardial epithelial to mesenchymal transitions in heart development and disease. Circ. Res. 110, 1628-1645 (2012).
50. Tanaka, Y. et al. Circulation-independent differentiation pathway from extraembryonic mesoderm toward hematopoietic stem cells via hemogenic angioblasts. Cell Rep. 8, 31-39 (2014).
51. Singh, B. N. et al. Hedgehog signaling during appendage development and regeneration. Genes (Basel) 6, 417-435 (2015).
52. Kim, P. G. et al. Signaling axis involving Hedgehog, Notch, and Scl promotes the embryonic endothelial-to-hematopoietic transition. Proc. Natl Acad. Sci. USA 110, E141 E150 (2013).
53. Dyer, M. A., Farrington, S. M., Mohn, D., Munday, J. R. & Baron, M. H. Indian hedgehog activates hematopoiesis and vasculogenesis and can respecify prospective neurectodermal cell fate in the mouse embryo. Development 128, 1717-1730 (2001).
54. Hochman, E., Kinston, S., Harmelin, A., Gottgens, B. & Izraeli, S. The SCL 3'=enhancer responds to Hedgehog signaling during hemangioblast specification. Exp. Hematol. 34, 1643-1650 (2006).
55. Pierre, M., Yoshimoto, M., Huang, L., Richardson, M. & Yoder, M. C. VEGF and IHH rescue definitive hematopoiesis in Gata-4 and Gata-6-deficient murine embryoid bodies. Exp. Hematol. 37, 1038-1053 (2009).
56. Li, Y. & Patra, J. C. Genome-wide inferring gene-phenotype relationship by walking on the heterogeneous network. Bioinformatics 26, 1219-1224 (2010).
57. Subramanian, A. et al. Gene set enrichment analysis: a knowledge-based approach for interpreting genome-wide expression profiles. Proc. Natl Acad. Sci. USA 102, 15545-15550 (2005).
58. Liu, F. et al. Induction of hematopoietic and endothelial cell program orchestrated by ETS transcription factor ER71/ETV2. EMBO Rep. 16, 654-669 (2015).
59. Banerji, C. R. S. et al. Cellular network entropy as the energy potential in Waddington's differentiation landscape. Sci. Rep. 3, 3039 (2013).
60. Downs, K. M. & Davies, T. Staging of gastrulating mouse embryos by morphological landmarks in the dissecting microscope. Development 118, 1255-1266 (1993).
61. Trapnell, C. et al. Differential gene and transcript expression analysis of RNAseq experiments with TopHat and Cufflinks. Nat. Protoc. 7, 562-578 (2012).
62. Brennecke, P. et al. Accounting for technical noise in single-cell RNA-seq experiments. Nat. Methods 10, 1093-1095 (2013).
63. Zeisel, A. et al. Cell types in the mouse cortex and hippocampus revealed by single-cell RNA-seq. Science 347, 1138-1142 (2015).
64. Wang, G., Kossenkov, A. V. & Ochs, M. F. LS-NMF: a modified non-negative matrix factorization algorithm utilizing uncertainty estimates. BMC Bioinformatics 7, 175 (2006).
65. Boutsidis, C. & Gallopoulos, E. SVD based initialization: a head start for nonnegative matrix factorization. Pattern Recogn. 41, 1350-1362 (2008).
66. Wehrens, R. & Buydens, L. M. C. Self- and super-organizing maps in R: the Kohonen package. J. Stat. Softw. 21, 1-19 (2007).
67. Tong, H. H., Faloutsos, C. & Pan, J. Y. Random walk with restart: fast solutions and applications. Knowl. Inf. Syst. 14, 327-346 (2008).
68. Page, L., Brin, S., Motwani, R. & Winograd, T. The PageRank Citation Ranking: Bringing Order to the Web ((Stanford InfoLab Publication Server, 1999).
69. Csardi, G. & Nepusz, T. The igraph software package for complex network research. Interjournal, Complex Systems 1695, 1-9 (2006).

All publications, patents, and patent applications mentioned in this specification are herein incorporated by reference to the same extent as if each individual publication, patent, or patent application was specifically and individually indicated to be incorporated by reference. In the event that the definition of a term incorporated by reference conflicts with a term defined herein, this specification shall control.

What is claimed is:

1. A non-transitory machine readable medium with instructions for analyzing cellular differentiation, the instructions, when executed by processing circuitry, cause the processing circuitry to perform operations comprising:
    receiving an expression profile matrix for a single cell RNA-seq dataset, the expression profile matrix having cells greater than 3,005;
    decomposing the expression profile matrix;
    quantitatively assessing the cellular state;
    prioritizing genes for progenitor and committed cellular states;
    assigning a metagene signature for an individual cell, and ranking cells with respect to specific cellular states including generating a heterogeneous metagene-metacell graph and using a random walk with restart process on the heterogeneous metagene-metacell graph.

2. The machine readable medium of claim 1, wherein decomposing the expression profile matrix includes identifying metagenes using weighted Poisson non-negative matrix factorization.

3. The machine readable medium of claim 1, wherein an expected gene expression level is modeled as a linear combination of non-negative metagene basis and coefficients.

4. The machine readable medium of claim 1, wherein an observed gene expression level is modeled as a mixture of Poisson distribution of expected expression level and a dropout event represented by a low-magnitude Poisson process.

5. The machine readable medium of claim 1, wherein decomposing the expression matrix includes approximating a product of non-negative metagene basis and coefficients.

6. The machine readable medium of claim 5, wherein the metagene basis corresponds to a contribution of each gene to each metagene.

7. The machine readable medium of claim 5, wherein the metagene coefficient corresponds to a probabilistic simplex that indicates the relative weight of each metagene in each cell.

8. The machine readable medium of claim 1, further including mapping cells into metacells using a self-organizing map (SOM).

9. The machine readable medium of claim 1 further including ranking genes for cellular states according to their expression profile.

10. The machine readable medium of claim 1, where prioritizing genes for progenitor and committed cellular states includes determining a measure of metagene entropy for cells.

11. The machine readable medium of claim 1 further including imposing a requirement in which the metagene expression profiles between cells in neighboring development stages are the same.

12. The machine readable medium of claim 11 includes using a self-organized map.

13. The machine readable medium of claim 12, wherein using the self-organized map includes correlating a hexagonal grid of the map with a cell expression pattern.

14. The machine readable medium of claim 13 further including clustering cells by partitioning the map.

15. The machine readable medium of claim 14 wherein a central cell of the map is correlated with an early progenitor.

16. The machine readable medium of claim 14, wherein a peripheral cell of the map is correlated with a mature cell.

17. The machine readable medium of claim 1, wherein prioritizing genes for progenitor and committed cellular states includes generating a transition matrix.

18. The machine readable medium of claim 8 including classifying a metacell as a progenitor of a neighboring metacell if the metagene entropy is higher than a derivative metacell.

19. The machine readable medium of claim 1 including using a random walk with restart (RWR) process on the heterogeneous graph to determine a probability of a metacell being in a committed state to one metagene, or being in a progenitor state with the ability to transition to multiple metagenes.

20. The machine readable medium of claim 8 including identifying a developmental trajectory based on a path length of the self-organized map.

* * * * *